US007264814B2

(12) United States Patent
Nishiyama

(10) Patent No.: US 7,264,814 B2
(45) Date of Patent: Sep. 4, 2007

(54) COMPOSITION AND METHOD FOR TREATING CANCER USING HERPES VIRUS

(75) Inventor: Yukihiro Nishiyama, 2-8-25, Shiratori, Togo-cho, Aichi-gun, Aichi 470-0155 (JP)

(73) Assignees: M's Science Corporation, Chuo-Ku, Kobe-shi, Hyogo (JP); Yukihiro Nishiyama, Aichi-gun, Aichi (JP)

(*) Notice: Subject to any disclaimer, the term of this patent is extended or adjusted under 35 U.S.C. 154(b) by 244 days.

(21) Appl. No.: 10/477,444

(22) PCT Filed: May 9, 2002

(86) PCT No.: PCT/JP02/04547

§ 371 (c)(1), (2), (4) Date: Nov. 7, 2003

(87) PCT Pub. No.: WO02/092826

PCT Pub. Date: Nov. 21, 2002

(65) Prior Publication Data

US 2004/0228876 A1 Nov. 18, 2004

(30) Foreign Application Priority Data

May 9, 2001 (JP) ............................ 2001-139094
Sep. 28, 2001 (JP) ............................ 2001-300931

(51) Int. Cl.
*A61K 39/12* (2006.01)

(52) U.S. Cl. .............................. 424/199.1; 424/229.1; 435/320.1

(58) Field of Classification Search ............ 424/199.1, 424/204.1, 229.1; 435/320.1, 69.1, 6
See application file for complete search history.

(56) References Cited

U.S. PATENT DOCUMENTS

| | | | | |
|---|---|---|---|---|
| 5,837,532 | A * | 11/1998 | Preston et al. | 435/320.1 |
| 5,922,328 | A * | 7/1999 | Spector et al. | 424/231.1 |
| 6,641,817 | B1 * | 11/2003 | Coffin et al. | 424/199.1 |

FOREIGN PATENT DOCUMENTS

| | | | |
|---|---|---|---|
| WO | WO96/04394 | * | 2/1996 |
| WO | WO98/42195 | | 10/1998 |

OTHER PUBLICATIONS

Pyles, R.B. and Thompson, R.L., "Evidence that the Herpes Simplex Virus Type 1 Uracil DNA Glycosylase is Required for Efficient Viral Replication and Latency in the Murine Nervous System", Journal of Virology, vol. 68, No. 8, Aug. 1994, pp. 4963-4972.

* cited by examiner

*Primary Examiner*—Ali R. Salimi
(74) *Attorney, Agent, or Firm*—Ivor R. Elrifi, Esq.; Mintz Levin Cohn Ferris Glovsky and Popeo PC

(57) ABSTRACT

The present invention provides a herpes virus in which a non-essential gene for replication is inactivated More particularly, the present invention provides a herpes virus in which a non-essential gene for replication present in a UL or US region is inactivated. More preferably, the non-essential gene for replication contains US3 or UL56. The herpes virus may be preferably a herpes simplex virus, and more preferably herpes simplex virus 1 or herpes simplex virus 2. The present invention provides a method, composition and use for treating various diseases or disorders including tumor and infectious diseases. The present invention also provides a method, composition and use for activating a prodrug.

9 Claims, 20 Drawing Sheets
(2 of 20 Drawing Sheet(s) Filed in Color)

*FIG. 13B*

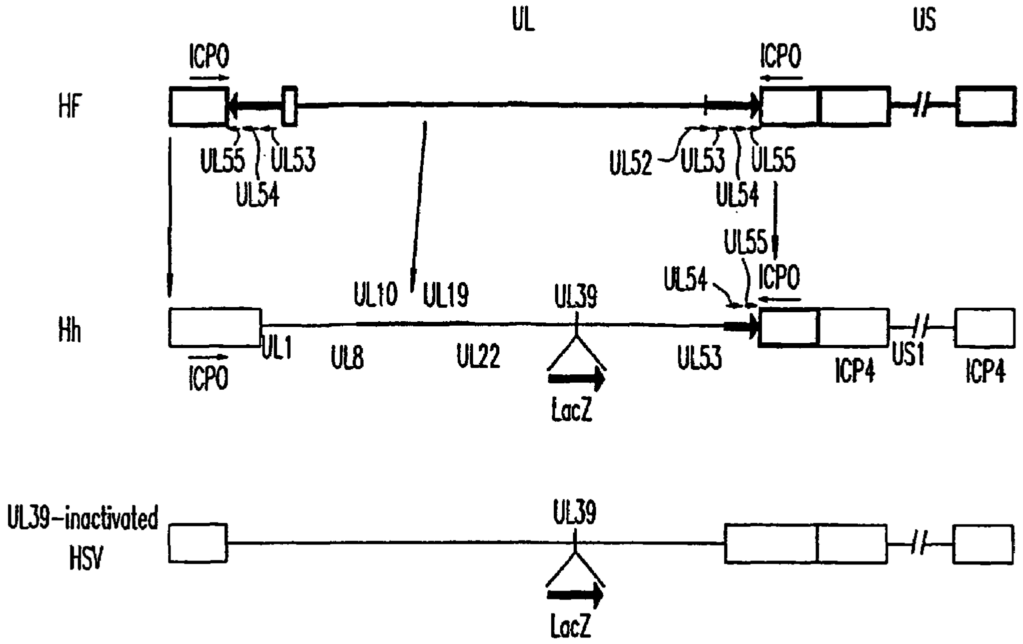

| | UL1 | | | | | | | | | | | | UL6 | | | UL8 | | | |
|---|---|---|---|---|---|---|---|---|---|---|---|---|---|---|---|---|---|---|---|
| | 261 | 269 | 273 | 294 | 299 | 310 | 327 | 343 | 489 | 503 | 511 | 541 | 1149 | 1197 | 1338 | 289 | 354 | 397 | 560 |
| HF | C | G | G | G | G | T | T | G | C | T | A | T | G | T | G | G | A | C | C |
| Hh | T | A | A | A | T | C | C | A | A | C | G | C | T | G | A | A | C | G | T |
| hrR3 | T | A | A | A | T | C | C | A | A | C | G | C | T | G | A | A | C | G | T |

| | UL10 | | | | | | | UL12 | | | | | | UL19 |
|---|---|---|---|---|---|---|---|---|---|---|---|---|---|---|
| | 466 | 482 | 608 | 618 | 633 | 645 | 762 | 601 | 643 | 661 | 802 | 828 | 943 | 1152 |
| HF | C | T | T | C | C | C | C | T | A | T | T | G | T | A |
| Hh | C | T | T | C | C | C | C | T | A | T | T | G | T | A |
| hrR3 | T | C | C | T | T | A | A | C | G | C | C | A | C | G |

| | UL22 | UL26 | | | | | | UL29 | UL44 | | | UL51 | UL53 | | | | | |
|---|---|---|---|---|---|---|---|---|---|---|---|---|---|---|---|---|---|---|
| | 1393 | 1410 | 1467 | 1492 | 1512 | 1569 | 1704 | 2095 | 544 | 713 | 788 | 617 | 1044 | 1060 | 1098 | 1107 | 1120 | 1134 |
| HF | G | T | A | A | G | A | A | A | G | T | C | G | T | T | T | C | G | C |
| Hh | A | G | G | C | A | G | G | G | A | C | T | A | G | C | T | T | T | T |
| hrR3 | A | G | G | C | A | G | G | G | A | C | T | A | G | C | C | T | T | T |

| | UL54 | | UL55 | ICP0 | | | | US1 | | | | | US3 | | | | | | ICP4 |
|---|---|---|---|---|---|---|---|---|---|---|---|---|---|---|---|---|---|---|---|
| | 1155 | 118 | 65 | 2395 | 2427 | 2445 | 2471 | 347 | 399 | 483 | 494 | 516 | 118 | 184 | 189 | 222 | 360 | 406 | 2770 |
| HF | T | G | - | G | - | - | G | A | G | A | T | A | A | A | G | T | T | T | A |
| Hh | T | G | - | G | - | - | G | G | T | C | C | C | G | G | T | G | C | C | G |
| hrR3 | G | A | C | A | G | A | A | G | T | C | C | C | G | G | T | G | C | C | G |

| | | | |
|---|---|---|---|
| UL19 1094-1560 | ICP0 2082-2517 | UL1 245-542 | UL51 403-62 |
| UL22 1057-1516 | US1 308-736 | UL6 1088-1461 | UL53 952-R309 |
| UL26 1405-1819 | US3 89-458 | UL8 275-724 | UL54 1128-1362 |
| UL29 2028-2297 | ICP4 2540-2951 | UL10 301-782 | UL54 R97-187 |
| | | UL12 554-1017 | UL55 R101-164 |

*FIG. 13D*

```
5460
        10         20         30         40         50         60
gggagcaggg ggcgtcgacc cgggacgagg gaaaacaata agggacgccc cccgtgtttg
lyGluGlnGl yAlaSerThr ArgAspGluG lyLysGln** *
                       ICPO termination codon

        70         80         90        100        110        120
tggggagggg ggggtcgggc gctgggtggt ctctggccgc gcccactaca ccagccaatc

       130        140        150        160        170        180
cgtgtcgggg aggggaaaag tgaaagacac gggcaccaca caccagcggg tctttagtgt

       190        200        210        220        230        240
tggccctaat aaaaaaaaac tcaggggatt tttgctgtct attgggaaat aaaggtttac

       250        260        270        280        290        300
ttttgtatct tttccctgtc tgtgttggat ggatctcggg ggtgcgtggg agtgggggtg

       310        320        330        340        350        360
cgtgggagtg ggggtgcgtg ggagtgaggg tgcgtgggag tgagggtgcg tgggagtggg

       370        380        390        400        410        420
ggtgcgtggg agtgggggtg cgtgggagtg ggggtgcgtg ggagtggggg tgcgtgggag

       430        440        450        460        470        480
tgggggtgac atgttgggca ggctctggtg ttaaccacag agtcgcggcc cgggctgcct

       490        500        510        520        530        540
gaccaccgat ccccgaaagc atcctgccac tggcatggag ccagaaccac agtgggttgg

5460                         6024
       550        560             580        590        600
gtgtgggtgt taagtttccg cgagcgcctg cccgCCGAGG CTATGTCGGA CCACCCCCCA
                                   116514 5' of insertion

       610        620        630        640        650        660
ACCTATGCCA CTGTCGTGGC CGTTCGTTCG ACCGAACAGC CGTCCGGGGC TTTGGCGCCC

       670        680        690        700        710        720
GACGACCAGC GACGAACGCA AAACTCGGGC GCGTGGCGGC CTCCTAGGGT CAATTCGCGC

       730        740        750        760        770        780
GAGCTGTACA GGGCCCAACG CGCAGCGCGC GGCTCGTCTG ATCATGCCCC ATACCGGCGA
                                          *** *
                       UL56 termination codon

       790        800        810        820        830        840
CAGGGCTGTT GTGGTGTGGT GGGGCGCCAT GCTGTATTTG GGGTGGTCGC GATAGTGGTG

       850        860        870        880        890        900
GTCATTATTC TGGTATTCCT GTGGCGGTAA GCGCCCCTGT GAGTTAATAA ATAAAAGTAT
                                                           116191
```

```
         10         20         30         40         50         60
GCCTGTCCCG TGGGGACCAT GGAtATCCGG TAGACGGGCA GGGGAGTCTG CACCGCCGCA

         70         80         90        100        110        120
TTACGGATAA GCGCCGCGAT CGCCGGGGGT GTGGTGCCCT GCTGTTCCGT GGCGGCCAGT

        130        140        150        160        170        180
CTCAGGAGGC GCTTGACAAT TCCGCAGGTC TGTGGGGGCG GCGTGCCGCC CGCCGTGTCC
<------------------------------ UL52 ------------------------------
                110488
        190        200        210        220        230        240
TCCCCGGGAC TGGCGGGccc ccgtcgcggg tgtttgtgtt tgtttattcc gacattggtt
================
3' of insertion  8420                                          8363
        250        260        270        280        290        300
tatttaaata aacacagccg ttctgcgtgt ctgttcttgc gtgtggctgg gggcttatat

        310        320        330        340        350        360
gtggggtccc gggggcggga tggggtttag cggcgggggg cggcgcgccg gacggggcgc
                                                                8483
```

FIG. 13F

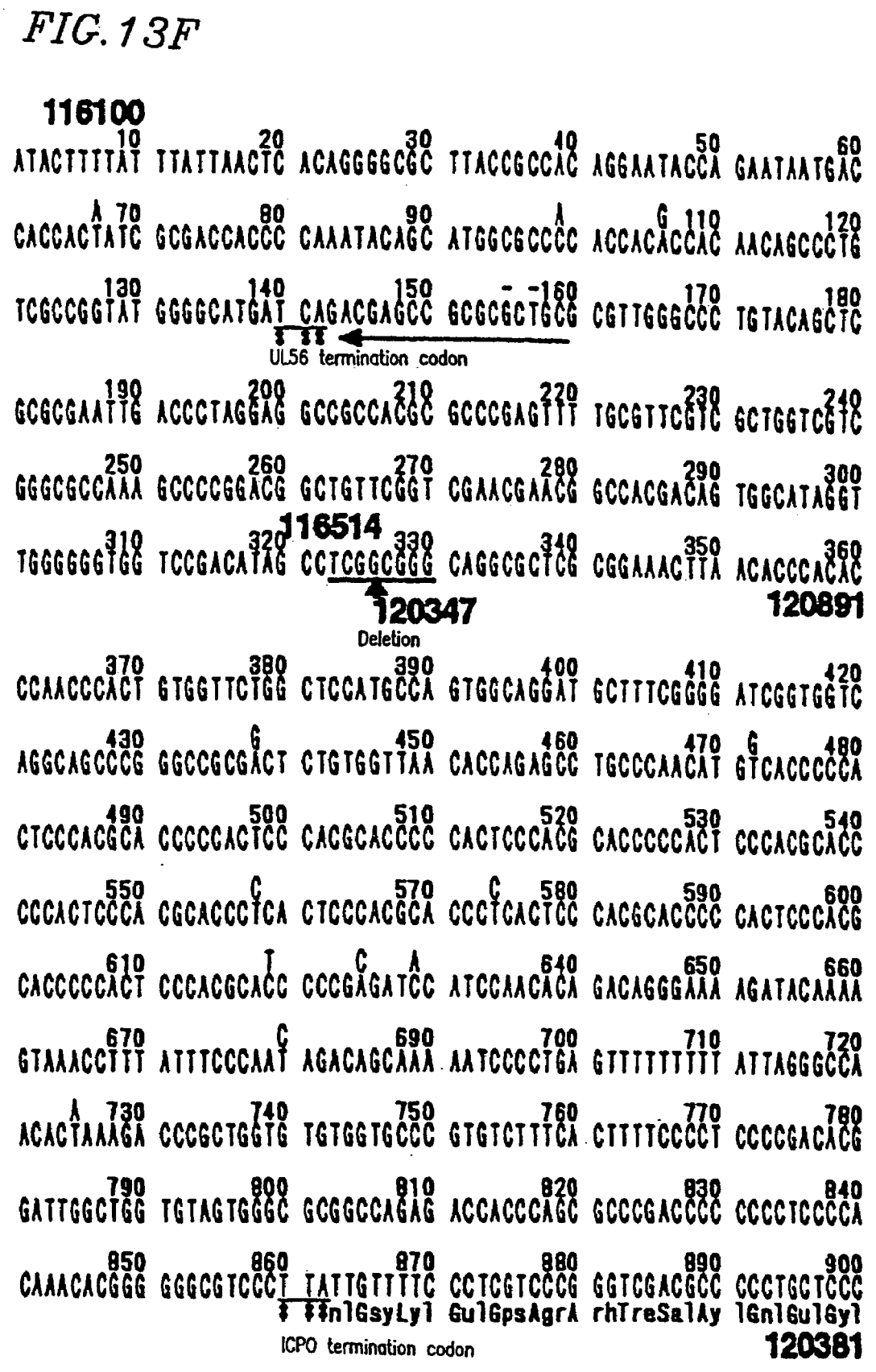

```
          10         20         30         40         50         60
ATACTTTTAT TTATTAACTC ACAGGGGCGC TTACCGCCAC AGGAATACCA GAATAATGAC
```

```
       A  70         80         90       A           G 110        120
CACCACTATC GCGACCACCC CAAATACAGC ATGGCGCCCC ACCACACCAC AACAGCCCTG
```

```
         130        140        150      --160        170        180
TCGCCGGTAT GGGGCATGAT CAGACGAGCC GCGCGCTGCG CGTTGGGCCC TGTACAGCTC
                      ↑↑↑ ←
                    UL56 termination codon
```

```
         190        200        210        220        230        240
GCGCGAATTG ACCCTAGGAG GCCGCCACGC GCCCGAGTTT TGCGTTCGTC GCTGGTCGTC
```

```
         250        260        270        280        290        300
GGGCGCCAAA GCCCCGGACG GCTGTTCGGT CGAACGAACG GCCACGACAG TGGCATAGGT
```

```
         310    116514 330                340         350        360
TGGGGGGTGG TCCGACATAG CCTCGGCGGG CAGGCGCTCG CGGAAACTTA ACACCCACAC
                       ↑
                     120347                                   120891
                    Deletion
```

```
         370        380        390        400        410        420
CCAACCCACT GTGGTTCTGG CTCCATGCCA GTGGCAGGAT GCTTTCGGGG ATCGGTGGTC
```

```
         430      G  450        460        470      G  480
AGGCAGCCCG GGCCGCGACT CTGTGGTTAA CACCAGAGCC TGCCCAACAT GTCACCCCCA
```

```
         490        500        510        520        530        540
CTCCCACGCA CCCCCACTCC CACGCACCCC CACTCCCACG CACCCCCACT CCCACGCACC
```

```
         550       C  570       C  580        590        600
CCCACTCCCA CGCACCCTCA CTCCCACGCA CCCTCACTCC CACGCACCCC CACTCCCACG
```

```
         610     T     C     A        640        650        660
CACCCCCACT CCCACGCACC CCCGAGATCC ATCCAACACA GACAGGGAAA AGATACAAAA
```

```
         670        C  690        700        710        720
GTAAACCTTT ATTTCCCAAT AGACAGCAAA AATCCCCTGA GTTTTTTTTT ATTAGGGCCA
```

```
       A  730        740        750        760        770        780
ACACTAAAGA CCCGCTGGTG TGTGGTGCCC GTGTCTTTCA CTTTTCCCCT CCCCGACACG
```

```
         790        800        810        820        830        840
GATTGGCTGG TGTAGTGGGC GCGGCCAGAG ACCACCCAGC GCCCGACCCC CCCTCCCCA
```

```
         850        860        870        880        890        900
CAAACACGGG GGGCGTCCCT TATTGTTTTC CCTCGTCCCG GGTCGACGCC CCCTGCTCCC
                          ↑ ↑↑nlGsyLyl GulGpsAgrA rhTreSalAy lGnlGulGyl
                       ICP0 termination codon                        120381
```

COMPOSITION AND METHOD FOR TREATING CANCER USING HERPES VIRUS

TECHNICAL FIELD

The present invention relates to a novel herpes simplex virus (hereinafter may be herein abbreviated as HSV) construct. More specifically, the present invention relates to a method, use and a composition for treatment, therapy, or prevention of various diseases or disorders (e.g., cancer, bacterial infectious diseases, viral infectious diseases, and the like) using a novel herpes virus construct.

BACKGROUND ART

The first record of herpes virus in history dates back to the ancient Greece era before Christ. Herpes virus infrequently develops after primary infection, but hides in ganglia or the like for a long time. When the immune ability of a human is reduced, the virus is activated and proliferates to develop symptoms. In this case, herpes virus targets a wide range of tissues, such as skin, genital organs, eye ball, nerves, and the like. Even though antibodies which neutralize the virus are present in blood, symptoms often appear. It is thus believed that a reduction in cellular immune function is involved in the onset of symptoms.

Examples of herpes virus transmissible to a human include herpes simplex virus (HSV-1), herpes simplex virus (HSV-2), varicella zoster virus (VZV), EB virus (EBV), cytomegalovirus (HCMV), human herpes virus 6 (HHV-6), human herpes virus 7 (HHV-7), human herpes virus 8 (HHV-8), and the like.

HSV-1 causes gingivostomatitis or herpes facialis as a symptom of primary infection, and herpes labialis, herpes keratoconjunctivitis, herpes encephalitis as a symptom of recurrent infection. A major latent infection site of HSV-1 is trigeminal ganglia. HSV-2 causes genital herpes as a symptom of primary infection and genital herpes or neonatal herpes as a symptom of recurrent infection. A major latent infection site of HSV-2 is sacral ganglia. VZV causes chickenpox (varicella) as a symptom of primary infection and chickenpox and herpes zoster as a symptom of recurrent infection. A major latent infection site of VZV is dorsal root ganglion. EBV causes no symptom or causes infectious mononucleosis as a symptom of primary infection and Burkitt's lymphoma, or rhinopharyngeal cancer as a symptom of recurrent infection. A major latent infection site of EBV is B cell. HCMV causes no symptom as a symptom of primary infection and causes pneumonia, cytomegalic inclusion disease or the like as a symptom of recurrent infection. Latent infection sites of HCMV are believed to be macrophage and blood progenitor cells. HHV-6 causes exanthema subitum as a symptom of primary infection and exanthema subitum (pneumonia) as a symptom of recurrent infection. Latent infection sites of HHV-6 are believed to be macrophage and blood progenitor cells. HHV-7 causes exanthema subitum as a symptom of primary infection. A major latent infection site of HHV-7 is T cells. HHV-8 causes no symptom as a symptom of primary infection and causes Kaposi's sarcoma, PEL, and Castleman's disease as a symptom of recurrent infection. A major latent infection site of HHV-8 is B cells. Thus, a variety of infectious diseases are caused by herpes viruses.

An attenuated live vaccine against chickenpox virus is the only successful human herpes virus vaccine (Takahashi M., et al., Lancet, 2:1288, 1974). However, this attenuated live virus was accidentally obtained and is based on the characteristic that chickenpox is more effective to humoral immunity since it causes systemic infection due to viremia, unlike other herpes viruses. Therefore, a vaccine which can be universally utilized for herpes viruses is not yet available.

HSV is a representative herpes virus which is infectious to a human. HSV infection results from inoculation of the virus to mucosa, or the virus invading through a break in the skin. Most primary infections occur in the neonatal periods, but most children with a primary infection quickly improve. HSV is transmitted to a baby from an infected nurser or more generally an infected mother (specifically, a baby encounters genital herpes as the baby passes through the birth canal). In this case, HSV infection causes serious symptoms. For example, disseminated neonatal herpes infection causes hepatitis or the like, so that a baby may die.

Once HSV is acquired in the body, HSV is held in the body over a lifetime. During the latency period, HSV is localized in neurons in sensory ganglia (in the case of facial lesions, trigeminal ganglia are usually involved), and an infected patient is a symptomatic. However, HSV is activated by stimuli, such as menstruation, excessive exposure to sunlight or cold wind, pituitary gland or adrenal gland hormones, allergic reactions, or fever. The activated HSV is replicated and takes over the mechanism of a host cell, producing infectious mature virus particles and causing cell death. Symptoms caused by such a recurrent attack often appear on the mouth, face, and genital organs. For example, keratitis due to recurrent HSV is considered to be a major cause of blindness. Further, HSV infection to genital organs is frequent, and the incidence of sexually transmitted diseases (e.g., genital herpes) caused by HSV is significantly high. More specifically, examples of recurrent HSV-induced diseases which are caused by the recurrent attack include mucocutaneous diseases, such as herpes labialis (a disorder on the lips usually called "fever blister" or "cold sore"), gingivostomatitis (the mouth and gingiva are covered with vesicles and the vesicles rupture to form ulcers), pharyngitis, tonsillitis, keratoconjunctivitis (keratitis or inflammation of the cornea, which progresses to dendriform ulcer and eventually to cicatrization of the cornea, resulting in blindness), and genital herpes. In rare cases, HSV infection causes encephalitis, eczema herpeticum, traumatic herpes, and hepatitis.

Herpes simplex virus 2 (hereinafter also referred to as HSV-2) induces skin mucosa infection in genital organs. After infection, virus is maintained in the sensory ganglia, and then activated to cause recurrent HSV infection (Price, R. W., Walz, M. A., Wohlenberg, C., and Notkins, A. L. (1975) "Latent infection of sensory ganglia with herpes simplex virus: efficacy of immunization", Science 188, 938-940). Many researchers have extensively studied immune reactions with HSV-2 infection using animal models.

It has been reported that a major antigen-presenting cell (APC) is the dendritic cell (DC), including Langerhans cell (LC), and a number of macrophages (Mϕ) and B cells in the vagina (Parr, M. B., and Parr, E. L. (1991), "Langerhans cells and T lymphocyte subsets in the murine vagina and cervix", Biol. Reprod. 44:491-498; Nandi, D., and Allison, J. P. (1993), "Characterization of neutrophiles and T lymphocytes associated with the murine vaginal epithelium", Reg. Immunol., 5, 332-338).

It has been reported that T cells play an important role as a cytotoxic T lymphocyte (CTL), and produce antiviral cytokines against HSV-2 infection (Milligan, G. N., and Bernstein, D. I. (1995), "Analysis of herpes simplex virus-specific T cells in the murine female genital tract following genital infection with herpes simplex virus type 2", Virology 212, 481-489.; Parr, M. B., and Parr, E. L. (1998), "Mucosal immunity to herpes simplex virus type 2 infection in the mouse vagina is impaired by in vivo depletion of T lymphocytes", J. Virol. 72, 2677-2685; Milligan, G. N., Bernstein, D. I., and Bourne, N. (1998), "T lymphocytes are required for protection of the vaginal mucosae and sensory ganglia of immune mice against reinfection with herpes simplex virus type 2", J. Immunol. 160, 6093-6100).

It has been reported that mutants lacking replication capability can elicit a wide spectrum of immune reactions (Morrison, L. A., Da Costa, X. J., and Knipe, D. M. (1998), "Influence of mucosal and parenteral immunization with a replication-defective mutant of HSV-2 on immune responses and protection from genital infection", Virology 243, 178-187: McLean, C. S., Ni Challanain, D., Duncan, I., Boursnell, M. E. G., Jennings, R., and Inglis, S. C. (1996), "Induction of a protective immune response by mucosal vaccination with a DISC HSV-1 vaccine", Vaccine 14, 987-992).

It is known that infection with attenuated HSV-2 causes the flow of HSV-2-specific T cell type 1 (TH1)-like $CD4^+$ cells into the vagina (Milligan, G. N., Bernstein, D. I., and Bourne, N. (1998), "T lymphocytes are required for protection of the vaginal mucosae and sensory ganglia of immune mice against reinfection with herpes simplex virus type 2", J. Immunol. 160, 6093-6100).

However, in the pathology of HSV diseases, a detailed relationship between the role of a HSV-specific virus gene and immune reactions has not been fully clarified.

Thus, under the present circumstances, there is no decisive method for preventing or treating diseases or disorders caused by herpes viruses.

As a cancer therapy, there are generally surgical excision, chemotherapy, radiation therapy, and the like at present. However, none of these therapies have a sufficient effect on some types of cancers. For example, in the case of progressive pancreatic cancer and progressive ovarian cancer, a favorable prognosis is not obtained. Particularly, when progressive pancreatic cancer or progressive ovarian cancer is disseminated to peritonea, prognosis after surgical excision is likely to fall short of expectations.

Therefore, an attempt is being made to develop gene therapy as a new method for treating cancer. The following gene therapies against cancer are being studied: (1) a method for inhibiting the growth of tumor cells by controlling oncogenes using antisense or ribozyme, or by introducing antioncogenes; (2) a method for introducing a metabolically toxic gene (suicide gene) into tumor cells to cause them to commit suicide: (3) a method for enhancing anti-tumor immunity by introducing genes; (4) a method for protecting bone marrow stem cells using multidrug-resistant genes for the purpose of improving the effect of chemotherapy; and the like.

As a method of (2) as listed above, a method which employs the thymidine kinase of herpes simplex virus as a suicide gene is known. For example, the thymidine kinase of herpes simplex virus is introduced into cancer cells, and thereafter, ganciclovir is administered. The ganciclovir is phosphorylated by the thymidine kinase of herpes simplex virus to be activated. The activated ganciclovir inhibits the DNA polymerase of cancer cells. Therefore, by introducing the thymidine kinase of herpes simplex virus into cancer cells, the growth of the cancer cells can be suppressed, and it is also possible that the cancer cells are completely destroyed.

Since herpes simplex virus is a pathogenic virus, wild-type HSV cannot be used for cancer therapy. Therefore, research is directed to the use of attenuated herpes simplex viruses for cancer therapy (WO96/39841).

Therefore, an attempt has been made to use gene therapy as a novel therapy for cancer. As an example of such a gene therapy, a metabolically toxic gene (suicide gene) is introduced into tumor cells which are caused to commit suicide. More specifically, a method using the thymidine kinase of herpes simplex virus as a suicide gene is known.

As described above, herpes virus, such as herpes simplex virus (e.g., herpes virus type 1 (HSV-1) capable of replication), may mediate the destruction of tumor cells. Therefore, the use of a genetically engineered HSV-1 virus vector capable of replication is studied in association with antitumor therapy.

As such a HSV-1 virus vector, a γ34.5-deficient strain which lacks the γ34.5 gene (γ34.5) and therefore has a reduced level of neurotoxicity has been used, so that a certain level of its antitumor effect was demonstrated. However, the γ34.5-deficient strain has not yet become practical.

The present inventors have concentrated on a gene encoding US2 of HSV-2 (hereinafter abbreviated as US2 gene) and a gene encoding US3 of HSV-2 (hereinafter abbreviated as US3 gene), and investigated the pathological roles of these genes using a US2-deficient mutant or a US3-deficient HSV gene recombinant. As a result, the present inventors revealed that neither the US2 nor US3 gene is necessarily essential for the replication of the respective viruses in cell culture, and the US3-deficient HSV gene recombinant is significantly attenuated (Nishiyama, Y., Yamada, Y., Kurachi, R., and Daikoku, T (1992), "Construction of a US3 lacZ insertion Mutant of herpes simplex virus type 2 and characterization of its phenotype in vitro and in vivo", Virology 190, 256-268; Daikoku, T., Yamashita, Y., Tsurumi, T., Maeno, K., and Nishiyama, Y (1993), "Purification and biological characterization of the protein kinase encoded by the US3 gene of herpes simplex virus type 2", Virology 197, 685-694; Jiang, Y-H., Yamada, H., Goshima, F., Daikoku T., Oshima, S., Wada, K., and Nishiyama, Y (1998), "Characterization of the herpes simplex virus type 2 (HSV-2) US2 gene product and a US2-deficient HSV-2 mutant", J. Gen. Virol. 79, 2777-2784).

Previous research on genital herpes using murine models revealed that unlike infection with HSV-1 strain KOS, intravaginal infection with highly virulent HSV-2 strain 186 fails to induce increases in activated T cells within the vagina or a rapid increase of APC (antigen-presenting cell) in the early phase of infection (Inagaki-Ohara K, Daikoku T, Goshima F, Nishiyama Y, "Impaired induction of protective immunity by highly virulent herpes simplex virus type 2 in a murine model of genital herpes", Arch Virol. 2000; 145 (10): 1989-2002.).

Therefore, the objective of the present invention is to provide a characteristic-modified herpes virus construct, the use thereof, or a method using the same so as to treat or prevent diseases or disorders associated with herpes virus, or other diseases or disorders.

DISCLOSURE OF THE INVENTION

The present invention provides a herpes virus in which a non-essential gene for replication is inactivated. More particularly, the present invention provides a herpes virus in which a non-essential gene for replication present in UL and US regions are inactivated. The present invention also provides a herpes virus in which a gene not involved in DNA and deoxyribonucleotide metabolism is inactivated. More preferably, the non-essential gene for replication contains US3 and UL56. The herpes virus may be preferably a herpes simplex virus, and more preferably herpes simplex virus 1 or herpes simplex virus 2. The present invention provides a method, composition and use for treating various diseases or disorders including tumor and infectious diseases The present invention also provides a method, composition and use for activating a prodrug.

According to one aspect of the present invention, a herpes virus is provided in which at least one non-essential gene for replication thereof is inactivated.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11 and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

In one embodiment of this invention, the non-essential gene for replication contains UL56 or US3.

In one embodiment of this invention, the non-essential gene for replication contains UL39 and UL40.

In one embodiment of this invention, the non-essential gene for replication contains UL39 and UL56.

In one embodiment of this invention, the non-essential gene for replication contains UL2 and US3.

In one embodiment of this invention, the non-essential gene for replication contains UL56.

In one embodiment of this invention, the non-essential gene for replication contains US3.

In one embodiment of this invention, at least two non-essential genes for replication are inactivated.

In one embodiment of this invention, the second non-essential gene for replication and thereafter are selected from the group consisting of RL1, RL2, ORFP, ORFO, RL3, UL2, UL3, UL4, UL7, UL10, UL11, UL12, UL13, UL16, UL20, UL20.5, UL21, UL24, UL39, UL40, UL41, UL43, UL43.5, UL44, UL45, UL46, UL47, UL56, UL51, UL55, UL56, US1, US1.5, US2, US3, US4, US5, US7, US8, US8.5, US9, US10, US11 and US12.

In one embodiment of this invention, the herpes virus further comprises an exogenous suicide gene.

In one embodiment of this invention, the herpes virus further comprises a carboxyesterase gene.

In one embodiment of this invention, the virus has ability to select cancer cells.

In one embodiment of this invention, the inactivation includes at least one nucleotide substitution, addition, deletion or modification in the sequence of the non-essential gene for replication.

In one embodiment of this invention, the virus is a modified herpes simplex virus.

In one embodiment of this invention, the virus is a modified HSV-1 or HSV-2.

According to another embodiment of the present invention, a pharmaceutical composition comprises a herpes virus wherein at least one non-essential gene for replication thereof is inactivated, and a pharmaceutically acceptable carrier.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, US1, US2, US4, US5, US7, US8, US8.5, US9, US10, US11 and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

In one embodiment of this invention, the non-essential gene for replication contains UL56 or US3.

In one embodiment of this invention, the inactivation includes at least one nucleotide substitution, addition, deletion or modification in the sequence of the non-essential gene for replication.

In one embodiment of this invention, a signal for stopping translation is inserted into the sequence of the non-essential gene for replication.

In one embodiment of this invention, the signal for stopping translation is a polyadenylation signal.

In one embodiment of this invention, the virus is a modified herpes simplex virus.

In one embodiment of this invention, the virus is a modified HSV-1 or HSV-2.

In one embodiment of this invention, the pharmaceutical composition further comprises a prodrug capable of converting the attenuated herpes virus into an active form.

In one embodiment of this invention, the prodrug is selected from the group consisting of ganciclovir, acyclovir, taxol, and camptothecin.

In one embodiment of this invention, the composition is used for treatment of tumor.

In one embodiment of this invention, the pharmaceutical composition further comprises at least one drug for treatment of tumor.

In one embodiment of this invention, the composition is used to enhance an anticancer action of the prodrug which is converted into an active form by the herpes virus.

In one embodiment of this invention, the composition is used for treatment of an infectious disease.

In one embodiment of this invention, the infectious disease is caused by a herpes virus.

In one embodiment of this invention, the pharmaceutical composition comprises a gene derived from a pathogen of the infectious disease.

In one embodiment of this invention, the pharmaceutical composition comprises L1BR1.

In one embodiment of this invention, the composition is in the form of a vaccine.

In one embodiment of this invention, the composition is an agent for treating or preventing a disease or disorder caused by infection of a herpes virus.

In one embodiment of this invention, the disease caused by the infection of a herpes virus is a sexually transmitted disease.

In one embodiment of this invention, the composition is used for treatment or prevention of an infectious disease.

In one embodiment of this invention, the pharmaceutical composition further comprises a pathogen of the infectious disease.

In one embodiment of this invention, the pathogen of the infectious disease is a virus or bacterium.

In one embodiment of this invention, the pathogen of the infectious disease is selected from the group consisting of HIV, influenza virus, and rotavirus.

In one embodiment of this invention, a method for treating or preventing an infectious disease or tumor, comprises the step of administering a pharmaceutical composition comprising a herpes virus, at least one non-essential gene for replication thereof being inactivated, and a pharmaceutically acceptable carrier, to a subject requiring the treatment or prevention.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11 and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

In one embodiment of this invention, the non-essential gene for replication contains US3 or UL56.

In one embodiment of this invention, the inactivation includes at least one nucleotide substitution, addition, deletion or modification.

In one embodiment of this invention, the herpes virus is a modified herpes simplex virus.

In one embodiment of this invention, the herpes virus is a modified HSV-1 or HSV-2.

In one embodiment of this invention, the method further comprises the step of administering a prodrug which is converted into an active form by a herpes virus.

In one embodiment of this invention, the prodrug is selected from the group consisting of ganciclovir, acyclovir, taxol, and camptothecin.

In one embodiment of this invention, the method comprises the step of administering at least one drug for treatment of tumor.

In one embodiment of this invention, the method further comprises the step of administering at least one drug for treatment of an infectious disease.

In one embodiment of this invention, the tumor is selected from the group consisting of ovarian cancer, liver cancer, pancreatic cancer, bladder cancer, urethra cancer, large intestine cancer, skin cancer, malignant melanoma, osteosarcoma, head and neck squamous cell carcinoma, and stomach cancer.

According to another aspect of the present invention, a method is provided for enhancing an anticancer action of a prodrug which is converted into an active form by a herpes virus. The method comprises the step of administering a pharmaceutical composition comprising a herpes virus, at least one non-essential gene for replication thereof being inactivated, and a pharmaceutically acceptable carrier to a subject requiring the enhancement of an anticancer action.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11, and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, ULSI, UL55, UL56, US1, US2, US3, US4, US5, US7, US8, US8.5, US9, US10, US11 and US12.

In one embodiment of this invention, the non-essential gene for replication contains US3 or UL56.

In one embodiment of this invention, the prodrug is selected from the group consisting of ganciclovir, acyclovir, taxol, and camptothecin.

In one embodiment of this invention, the herpes virus is a modified herpes simplex virus.

In one embodiment of this invention, the herpes virus is a modified HSV-1 or HSV-2.

According to another aspect of the present invention, a method for reducing the severity or infection rate of a herpes virus, comprises the step of administering a vaccine comprising a herpes virus, at least one non-essential gene for replication thereof is inactivated, to a subject requiring the treatment or prevention.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11, and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

In one embodiment of this invention, the non-essential gene for replication contains US3 or UL56.

In one embodiment of this invention, the herpes virus is a modified herpes simplex virus.

In one embodiment of this invention, the herpes virus is a modified HSV-1 or HSV-2.

According to another aspect of the present invention, use of a herpes virus for producing a pharmaceutical composition for treating or preventing tumor is provided. At least one non-essential gene for replication of the herpes virus is inactivated.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11, and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

In one embodiment of this invention, the non-essential gene for replication contains US3 or UL56.

In one embodiment of this invention, the herpes virus is a modified herpes simplex virus.

In one embodiment of this invention, the herpes virus is a modified HSV-1 or HSV-2.

According to another aspect of the present invention, use of a herpes virus for producing a pharmaceutical composition for enhancing an anticancer action of a prodrug which is converted into an active form by the herpes virus, is provided. At least one non-essential gene for replication of the herpes virus is inactivated.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11, and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, ULSI, UL55, UL56, US1, US2, US3, US4, US5, US7, US8, US8.5, US9, US10, US11 and US12.

In one embodiment of this invention, the non-essential gene for replication contains US3 or UL56.

In one embodiment of this invention, the herpes virus is a modified herpes simplex virus.

In one embodiment of this invention, the herpes virus is a modified HSV-1 or HSV-2.

According to another aspect of the present invention, use of a herpes virus for producing a pharmaceutical composition for reducing the severity or infection rate of a herpes virus, is provided. At least one non-essential gene for replication of the herpes virus is inactivated.

In one embodiment of this invention, the non-essential gene for replication is present in a UL region or a US region.

In one embodiment of this invention, the non-essential gene for replication is selected from the group consisting of UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11, and US12.

In one embodiment of this invention, the non-essential gene for replication is a gene not involved in DNA and deoxyribonucleotide metabolism.

In one embodiment of this invention, the gene not involved in DNA and deoxyribonucleotide metabolism is selected from the group consisting of UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

In one embodiment of this invention, the non-essential gene for replication contains US3 or UL56.

In one embodiment of this invention, the pharmaceutical composition is a vaccine.

In one embodiment of this invention, the herpes virus is a modified herpes simplex virus.

In one embodiment of this invention, the herpes virus is a modified HSV-1 or HSV-2.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A and 6D show the vaginal mucosae of mock-infected mice. FIGS. 6B and 6E show the vaginal mucosae of mice infected with wild type 186. FIGS. 6C and 6F show the vaginal mucosae of mice infected with L1BR1. G, H and I indicate histological changes in the vaginal walls of mice infected with wild type 186 (G), wild type YY2 (H) and L1BR1 (I) on day 5 after inoculation. It should be noted that A to I are microscopic photographs at a magnification of 100. A, B, C, G, H and I show heamatoxylin-eosin stain. D, E and F show detection of HSV antigens.

FIG. 13B is a diagram showing the structure of a genome used in Example 13. HF is HSV-1 in which the UL56 gene thereof is inactivated. Hh is HSV-1 in which the UL39 and UL56 genes thereof are inactivated. UL39-inactivated HSV is HSV-1 in which the UL39 gene is inactivated. A list of mutated bases is also shown.

FIG. 13D shows a gene sequence in the vicinity of the UL56 gene inserted between TRL and the UL region. FIG. 13E shows a gene sequence in the vicinity of the UL52 gene inserted between TRL and the UL region. FIG. 13F shows an inherent gene sequence in the vicinity of the UL56 gene.

BEST MODE FOR CARRYING OUT THE-INVENTION

Figure 1:
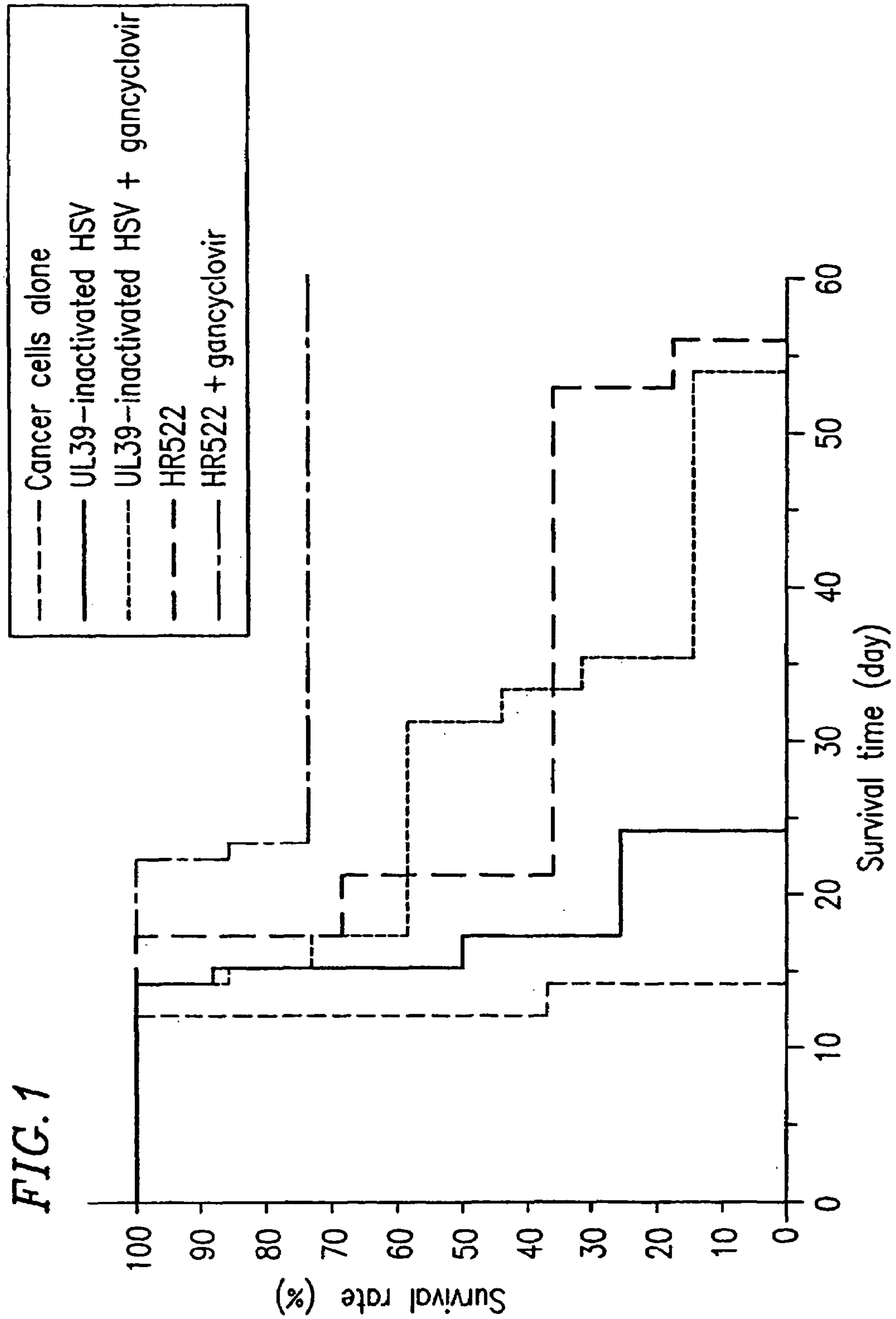
FIG. 1 is a graph showing a cancer treating effect obtained by inoculating an attenuated HSV according to the present invention.

It should be understood throughout the present specification that articles for a singular form (e.g., "a", "an", "the", etc. in English; "ein", "der", "das", "die", etc. and their inflections in German; "un", "une", "le", "la", etc. in French; "un", "una", "el", "la", etc. in Spanish, and articles, adjectives, etc. in other languages) include the concept of their plurality unless otherwise mentioned. It should be also understood that the terms as used herein have definitions typically used in the art unless otherwise mentioned. Documents, patents or patent applications cited herein are herein incorporated by reference in their entirety.

The term "herpes virus" as used herein refers to any viruses belonging to the family herpes virus. A herpes virus comprises about 162 capsomeres which include double helix DNA having a molecular weight of about $80\text{-}150\times10^6$ Da around a core protein. A herpes virus is characterized by latent infection. A herpes virus particle is in the shape of a sphere having a diameter of about 100-200 nm and has a regular icosahedron-like capsid of a diameter of around about 100 nm inside its envelope. The genome thereof is double-stranded DNA. The size of the genome is 152260 base pairs for herpes simplex virus type 1,172282 base pairs for EBVirus, 229400 base pairs for cytomegalovirus, for example. The virus is multiplied within a cell nucleus to form inclusion bodies which are positive to Feulgen reaction. The virus is multiplied well in a natural host, epithelial cells of an experimental animal, such as skin and mucosa, central nerve tissue, and the like. The family herpes virus is divided into three: the subfamily alpha herpes virus (e.g., human herpes virus 1 (herpes simplex virus type 1; HSV-1), human herpes virus 2 (herpes simplex virus type 2: HSV-2), Allerton virus, B virus, bovine mammilitis virus (BMV), feline rhinotracheitis virus, infectious laryngotracheitis virus ILT virus, varicella zoster virus (VZV), and the like); the subfamily beta herpes virus (e.g., cytomegalovirus, human herpes virus 6 (HHV-6), human herpes virus 7 (HHV-7), and the like); the subfamily gamma herpes virus (e.g., human herpes virus 4 (HHV-4), human herpes virus 8 (HHV-8), EBVirus (EBV), Marek's disease virus, and the like). Preferably, the herpes of the invention derived of the subfamily alpha herpes virus.

The term "herpes simplex virus" or "HSV" as used herein refers to any of viruses of the genus simplex virus of the subfamily alpha herpes virus of the family herpes virus. Herpes simplex virus is 100 to 200 mm in diameter and has an envelope containing a viral glycoprotein at its outermost layer, in which an icosahedral capsid is included. A construct called tegument is present between the capsid and the envelope, in which a number of viral proteins are contained. In the central portion (core)of the capsid, there is double-stranded DNA (about 150,000 base pairs). At least 74 genes are present in the genomic DNA, about half of which are non-essential genes for reproduction of cultured cells (accessory genes). Reproduction of genomic DNA and formation of the capsid are carried out within the nucleus. The capsid including DNA is transferred from the nucleus to the cytoplasm by budding from nuclear membrane. HSV includes two virus species called, representatively, type 1 (HSV-1) and type 2 (HSV-2), which are closely related to each other. A mutant of HSV-1 and HSV-2 is employed in the present invention. In some cases, HSV-2 is preferable. The term "attenuated HSV" as used herein refers to HSV whose toxicity is reduced by modification or the like.

The terms "non-essential gene for replication" and "accessory gene" are herein used interchangeably. Even if such a gene is absent in a virus, the growth of the virus is maintained. Such a gene is located in a UL region or US region and constitutes a unique gene in the genomic DNA. Preferable examples of such a gene include, but are not limited to, UL2, UL3, UL4, UL7, UL10, UL11, UL12, UL13, UL14, UL16, UL20, UL21, UL24, UL35, UL39, UL40, UL41, UL43, UL44, UL45, UL46, UL47, UL50, UL51, UL55, UL56, US1, US2, US3, US4, US5, US7, US8, US8.5, US9, US10, US11, US12, and the like for herpes simplex virus such as HSV-1 and HSV-2. For other herpes viruses, genes corresponding to the above-described genes may be inactivated.

In one embodiment, when a plurality of non-essential genes for replication are inactivated, the second gene and thereafter may be, but is not limited to, RL1, RL2, ORFP, ORFO, RL3, UL2, UL3, UL4, UL7, UL10, UL11, UL12, UL13, UL16, UL20, UL20.5, UL21, UL24, UL39, UL40, UL41, UL43, UL43.5, UL44, UL45, UL46, UL47, UL50, UL51, UL55, UL56, US1, US1.5, US2, US3, US4, US5, US7, US8, US8.5, US9, US10, US11, US12, and the like.

In a preferred embodiment, an example of the inactivated gene in the present invention is a gene which is not involved in DNA and deoxyribonucleotide metabolism. Although the present invention is not intended to be constrained by theory, inactivation of genes not involved in DNA and deoxyribonucleotide metabolism can dramatically increase safety and/or specificity to humans. Such genes not involved in DNA and deoxyribonucleotide metabolism, exclude the genes UL2, UL12, UL23, UL39, UL40 and UL50. Preferably, such genes not involved in DNA and deoxyribonucleotide metabolism lie in the US or UL region. Thus, genes not involved in DNA and deoxyribonucleotide metabolism include but are not limited to UL3, UL4, UL7, UL10, UL11, UL13, UL14, UL16, UL20, UL21, UL24, UL35, UL41, UL43, UL44, UL45, UL46, UL47, UL51, UL55, UL56, US1, US2, US3, US4, US5, US7, US8, US8.5, US9, US10, US11 and US12.

The attenuated HSV of the present invention can be multiplied favorably in cancer cells. Preferably, such a HSV has the ability to select a cancer cell.

An example of an attenuated HSV with at least one accessory gene inactivated is one whose UL39 or UL40 is inactivated. In this case, an attenuated HSV, in which UL39 or UL40 is inactivated along with at least one other accessory gene, is preferable.

The attenuated HSV in which UL39 or UL40 is inactivated must rely on a host for ribonucleotide reductase which is encoded by the inactivated gene, as it is required for DNA and deoxyribonucleotide metabolism. Therefore, when the attenuated HSV in which UL39 or UL40 is inactivated is inoculated into a cancer patient, the HSV can be multiplied favorably in vigorously dividing cancer cells. The cancer cells infected with such an attenuated HSV are suppressed from being multiplied due to the cytopathic effect of various proteins of the virus, potentially leading to their death.

When in addition to UL39 or UL40, at least one other accessory gene is inactivated, the virus can be multiplied favorably in cancer cells at substantially the same rate while the pathogenicity thereof to the host can be further reduced.

Examples of the attenuated HSV in which UL39 or UL40 and at least one other accessory gene are inactivated include an attenuated HSV in which UL39 (or UL40), UL55 and UL56 are inactivated, an attenuated HSV in which UL39 (or UL40) and UL2 are inactivated, an attenuated HSV in which UL39 (or UL40) and US3 are inactivated, an attenuated HSV in which UL39 (or UL40), UL2 and US3 are inactivated, and the like.

The attenuated HSV in which UL39 (or UL40), UL55 and UL56 are inactivated and the attenuated HSV in which UL39 (or UL40) and UL2 are inactivated have a higher level of safety than that of the attenuated HSV in which only UL39 (or UL40) is inactivated. The attenuated HSV in which UL39 (or UL40) and US3 are inactivated and the attenuated HSV in which UL39 (or UL40), UL2 and US3 are inactivated can cause apoptosis in a cancer cell as well as having a high level of ability to select cancer cells.

In another embodiment, a HSV in which US3 and/or UL56 is inactivated is provided.

The term "a gene is inactivated" as used herein indicates that at least one function of the gene is impaired, or preferably substantially eliminated. The method for inactivation is not particularly limited. Examples of such methods include the following known methods.

For example, a non-essential HSV gene for replication (e.g., US3 gene) is treated so as not to be translated (e.g., a promoter is altered so as not to be expressed); or a particular non-essential gene for replication out of the HSV genes (e.g., US3 gene) is subjected to recombination (e.g., insertion of another sequence, removal of a partial sequence, modification of bases, substitution of bases, and the like), so that the recombined gene is translated into a protein different from US3 (e.g., insertion of another sequence, removal of a partial sequence, modification of amino acids, substitution of amino acids, and the like).

A gene recombination process for preparing the above-described gene recombinants is not particularly limited. For example, a part or entirety of a particular non-essential gene for replication (e.g., US3 gene) is deleted; a part or entirety of a particular non-essential gene for replication is substituted; a part of a particular non-essential gene for replication is inverted, a part of the US3 gene is repeated; a part of a particular non-essential gene for replication is translocated; a gene fragment is inserted in a particular non-essential gene for replication so as to interrupt the particular non-essential gene for replication; and the like. Among them, deleting a part or entirety of a particular non-essential gene for replication, substituting a part or entirety of particular non-essential gene for replication, or inserting a gene fragment in a particular non-essential gene for replication so as to interrupt the particular non-essential gene for replication is preferable. Particularly, inserting a gene fragment in a particular non-essential gene for replication so as to interrupt the particular non-essential gene for replication is more preferable. Even more preferably, the gene fragment to be inserted contains a signal which stops translation. Among signals which stop translation, a polyadenylation signal derived from SV40 is preferable.

The term “protein”, “polypeptide” and “peptide” are herein used interchangeably and refer to a polymer consisting of a series of amino acids. The term “amino acid” refers to an organic molecule containing a carbon atom(s) with a carboxy group(s) and an amino group(s). An amino acid is herein preferably any of twenty naturally occurring amino acids but not limited to them.

A certain amino acid may be substituted with another amino acid without clear reduction or loss of interactive binding capability, for example, in a protein structure, such as a cationic region or a binding site for a substrate molecule. The biological function of a certain protein is determined by the interaction capability and properties of the protein. Therefore, even if substitution of a particular amino acid is performed in an amino acid sequence (or at the DNA code sequence level), a protein may maintain its original properties after the substitution. Therefore, peptides disclosed herein or DNA encoding the peptides may be modified in various manners without clearly impairing their biological utility.

When the above-described modifications are designed, the hydrophobicity indexes of amino acids may be taken into consideration. The hydrophobic amino acid indexes play an important role in providing a protein with an interactive biological function, which is generally recognized in the art (Kyte. J and Doolittle, R. F., J. Mol. Biol. 157(1):105-132, 1982). The hydrophobic property of an amino acid contributes to the secondary structure of a generated protein and then regulates interactions between the protein and other molecules (e.g., enzymes, substrates, receptors, DNA, antibodies, antigens, etc.). Each amino acid is given a hydrophobicity index based on the hydrophobicity and charge properties thereof as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid(−3.5): asparagine (−3.5); lysine (−3.9); and arginine (−4.5)).

It is well known that if a certain amino acid is substituted with another amino acid having a similar hydrophobicity index, a resultant protein may still have a biological function similar to that of the original protein (e.g., a protein having an equivalent enzymatic activity). For such an amino acid substitution, the hydrophobicity index is preferably within ±2, more preferably within ±1, and even more preferably within ±0.5. It is understood in the art that such an amino acid substitution based on the hydrophobicity is efficient. As described in U.S. Pat. No. 4,554,101, amino acid residues are given the following hydrophilicity indexes: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably ±1, and even more preferably ±0.5.

The term “conservative substitution” as used herein refers to amino acid substitution in which a substituted amino acid and a substituting amino acid have similar hydrophilicity indexes or/and hydrophobicity indexes. Examples of the conservative substitution include, but are not limited to, substitutions within each of the following groups: arginine and lysine; glutamic acid and aspartic acid; serine and threonine; glutamine and asparagine; and valine, leucine, and isoleucine, which are well known to those skilled in the art.

The term “nonconservative substitution” as used herein refers to substitution which is not a conservative substitution as described above and by which a function of a protein is altered. Examples of nonconservative substitution include, but are not limited to, substitution between each of the following groups: arginine and lysine; glutamic acid and aspartic acid; serine and threonine; glutamine and asparagine: valine, leucine, and isoleucine; and the like, which are well known to those skilled in the art.

To prepare functionally equivalent polypeptides, amino acid addition, deletion or modification can be performed other than amino acid substitution. Amino acid substitution means to substitute at least one amino acid (e.g., 1 to 10 amino acids, preferably 1 to 5 amino acids, and more preferably 1 to 3 amino acids) in an original peptide with the same number of other amino acids. Amino acid addition means to add at least one amino acid (e.g., 1 to 10 amino acids, preferably 1 to 5 amino acids, and more preferably 1 to 3 amino acids) to an original peptide chain. Amino acid deletion means to delete at least one amino acid (e.g., 1 to 10 amino acids, preferably 1 to 5 amino acids, and more preferably 1 to 3 amino acids) from an original peptide. Amino acid modification includes, but is not limited to, amidation, carboxylation, sulfation, halogenation, alkylation, glycosylation, phosphorylation, hydroxylation, acylation (e.g., acetylation), and the like. A substituted or added amino acid may be a naturally occurring amino acid, a non-naturally occurring amino acid, or an amino acid analog. A naturally occurring amino acid is preferable.

A nucleic acid molecule encoding the polypeptide of the present invention used herein may have base deletion (s) (a part of the nucleic acid sequence is deleted), substitution(s) (a part of the nucleic acid sequence is substituted with other bases), or addition(s) (a part of another nucleic acid sequence is added) as long as the expressed polypeptide has substantially the same activity as the polypeptide of the present invention, if the expressed peptide is intended to exhibit the same or similar function. Alternatively, another nucleic acid may be ligated to 5' end and/or 3' end. Further, a nucleic acid molecule which hybridizes to a gene encoding the polypeptide of the present invention under stringent conditions and which encodes a polypeptide having substantially the same function as that of the polypeptide of the present invention. A method for preparing such a nucleic acid molecule is known in the art and is used in the present invention.

A part of the nucleic acid sequence of the polypeptide of the present invention may be subjected to deletion or substitution, or a part of another nucleic acid sequence may be added to the nucleic acid sequence of the polypeptide so that the activity of the expressed polypeptide is substantially different from that of the original polypeptide or preferably eliminated, if the present invention is intended to modify, or preferably inactivate, a function of a polypeptide. Alternatively, another nucleic acid may be ligated to the 5' end and/or 3' end.

The term "expressibly incorporated" as used herein indicates that a suicide gene of interest is incorporated downstream of a promoter sequence described below, for example.

The attenuated HSV of the present invention can be obtained by inserting the above-described exogenous suicide gene downstream of a promoter sequence using a HSV vector into which the promoter sequence and a terminator sequence are incorporated so as to inactivate an accessory gene, for example.

A promoter is not particularly limited if the promoter functions as a promoter in tumor cells. A tumor-specific promoter and a HSV-derived promoter are preferable. Examples of such a promoter, which is also useful in practicing the present invention (particularly, in production of a gene vaccine for humans), include, but are not limited to, promoters derived from simian virus 40 (SV40 ), murine mammary gland tumor virus (MMTV), human immunodeficiency virus (HIV) (HIV long terminal repeat sequence (LTR) promoter), Moloney's virus, ALV, cytomegalovirus (CMV) (CMV immediate early promoter), Epstein-Barr virus (EBV), Rous sarcoma virus (RSV), and promoters from human genes, such as, human actin, human myosin, human hemoglobin, human muscular creatine, and human metallothionein.

A tumor cell-specific promoter includes a promoter which is induced selectively or at a high level in a particular type of cell or tumor cell, such as a cancer embryonal protein promoter (e.g., CEA, AFP, and the like), atyrosinase promoter, an albumin promoter, a stress-induced GRP78/Bip promoter, and the like.

Examples of a HSV-derived promoter include a HSV primary protein UL29 promoter, a HSV UL39 promoter, and the like.

Examples of a polyadenylation signal useful for practice of the present invention (particularly, in production of a gene vaccine for humans) include, but are not limited to, a bovine growth hormone polyadenylation signal, a SV40 polyadenylation signal, and a LTR polyadenylation signal. Particularly, a SV40 polyadenylation signal present in pCEP4 plasmid (Invitrogen, San Diego, Calif.; called SV40 polyadenylation signal) is employed.

In addition to control elements required for DNA expression, other elements may be included in a DNA molecule. A HSV-derived promoter used herein may further have an enhancer. The above-described additional elements include an enhancer. An enhancer may be selected from the group consisting of human actin, human myosin, human hemoglobin, human muscular creatine and virus enhancers, such as enhancers from CMV, RSV and EBV, but is not limited to them.

A gene construct may be provided with a mammalian replication origin so as to maintain the construct outside a chromosome and produce a large number of copies within a cell. Plasmids pCEP4 and pREP4 (Invitrogen, San Diego, Calif.) include the replication origin of Epstein-Barr virus and a nuclear antigen EB NA-1 code region which causes replication of large numbers of copies of the episome. In some embodiments, cDNA encoding an immunomodulatory protein is inserted within pCDNA3.

In some preferred embodiments, a nucleic acid molecule including a nucleotide sequence encoding the genes of a target protein, an immunomodulatory protein, and a protein which accelerates an immune response to the target protein, is delivered. An example of such a gene is a gene encoding a cytokine or a lymphokine, such as α-interferon, gamma-interferon, platelet-derived growth factor (PDGF), TNF, epidermal growth factor (EGF), IL-1, IL-2, IL-4, IL-6, IL-8, IL-10 and IL-12. In some embodiment, a gene construct used in a composition for immunization preferably includes the gene of GM-CSF.

To maximize protein production, a control sequence suitable for gene expression in a cell to which a gene construct is inserted may be selected. Further, a codon which is most efficiently transcribed in a cell may be selected. Those skilled in the art can easily produce a DNA construct which functions within a cell based on well-known techniques.

Such a nucleic acid can be obtained by a well-known PCR method, or chemically synthesized. These methods may be combined with a site specific mutagenesis method, a hybridization method, and the like.

The molecular biological methods, biochemical methods, and microbiological methods used herein are well known and commonly used in the art, as disclosed in, for example, Ausubel F. A. et al Ed. (1988), "Current Protocols in Molecular Biology", Wiley, New York, N.Y.; Sambrook J. et al., (1987) "Molecular Cloning: A Laboratory Manual". 2nd Ed., Cold Spring Harbor Laboratory Press, Cold Spring Harbor, N.Y.; Jikken Igaku [Experimental Medicine], "Experimental Methods for Gene Introduction & Expression Analysis", special issue, Yodo-sha, 1997; and the like.

The term "homology" of a gene refers to the magnitude of identity between two or more gene sequences. Therefore, the greater the homology between two certain genes, the greater the identity or similarity between their sequences. Whether or not two genes have homology is determined by comparing their sequences directly or by a hybridization method under stringent conditions. When two gene sequences are directly compared with each other, the genes have homology if representatively at least 50%, preferably at least 70%, more preferably at least 80%, 90%, 95%, 96%, 97%, 98%, or 99% of the DNA sequence of the genes are identical.

Comparison of identity between base sequences is herein calculated by BLAST which is a tool for analyzing a sequence using default parameters.

The term "polynucleotide hybridized under stringent conditions" as used herein refers to a polynucleotide hybridized under well-known conditions commonly used in the art. Such a polynucleotide can be obtained by a colony hybridization method, a plaque hybridization method, a Southern blotting hybridization method, or the like using a polynucleotide selected from the polynucleotides of the present invention as a probe. Specifically, such a polynucleotide can be identified by hybridization using a filter, on which DNA derived from a colony or a plaque is immobilized, in the presence of 0.7 to 1.0 M NaCl at 65° C., followed by washing the filter with SSC (saline-sodium citrate) solution having 0.1 to 2-fold concentration (SSC solution with 1 fold concentration contains 150 mM sodium chloride and 15 mM sodium citrate) at 65° C. Hybridization can be conducted in accordance with a method as described in an experimental manual, such as Molecular Cloning 2nd ed., Current Protocols in Molecular Biology, Supplement 1-38, DNA Cloning 1: Core Techniques, A Practical Approach, Second Edition, Oxford University Press (1995), and the like. Preferably, sequences hybridized under stringent conditions herein exclude sequences consisting only of A and sequences consisting only of T.

The term "hybridizable polynucleotide" as used herein refers to a polynucleotide which can hybridize to another polynucleotide under the above-described conditions for hybridization. Specific examples of hybridizable polynucleotides include a polynucleotide having at least 60% homology with the base sequence of DNA encoding a polypeptide having an amino acid sequence indicated by SEQ ID NO: 2, 4 or 6, more preferably a polynucleotide having at least 80% homology, and even more preferably at least 95%. Homology described herein is represented by similarity indicated by a score using BLAST which is a search program employing an algorithm developed by Altschul et al. (J. Mol. Biol. 215, 403-410 (1990)).

The term "derived oligonucleotide" or "derived polynucleotide" refers to an oligonucleotide or polynucleotide including a derivative of a nucleotide or having a linkage between nucleotides which is not normal. The above-described terms are interchangeably used. Specifically, examples of such an oligonucleotide include a derived oligonucleotide in which a phosphodiester bond is converted to a phosphothioate bond, a derived oligonucleotide in which phosphodiester bond is converted to N3'-P5' phosphoramidate bond, a derived oligonucleotide in which ribose and phosphodiester bond are converted to peptide-nucleic acid bond, a derived oligonucleotide in which uracil is substituted with C-5 propynyl uracil, a derived oligonucleotide in which uracil is substituted with C-5thiazole uracil, a derived oligonucleotide in which cytosine is substituted with C-5 propynyl cytosine, a derived oligonucleotide in which cytosine is substituted with phenoxazine-modified cytosine, a derived oligonucleotide in which ribose is substituted with 2'-O-propynyl ribose, a derived oligonucleotide in which ribose is substituted with 2'-methoxyethoxy ribose, and the like.

The term "amino acid" as used herein refers to any naturally occurring amino acid and non-naturally occurring amino acid as described above. The term "derivated amino acid" as used herein refers to an amino acid which is different from naturally occurring amino acids but has a function similar to that of its original naturally occurring amino acid. Such derivated amino acids are well known in the art.

The term "nucleotide" as used herein refers to any naturally occurring nucleotide and non-naturally occurring nucleotide. The term "derived nucleotide" as used herein refers to a nucleotide which is different from naturally occurring nucleotides but has a function similar to that of its original naturally occurring nucleotide. Such derived nucleotides are well known in the art.

The term "biological activity" as used herein refers to the activity which a certain factor (e.g., polypeptide or protein) has within an organism, including activity exhibiting various functions. For example, when the certain factor is an enzyme, its biological activity includes enzymatic activity. As another example, when the certain factor is a ligand, its biological activity includes binding to a receptor to which the ligand corresponds.

The term "variant" as used herein refers to a substance, such as polypeptide, polynucleotide, or the like, which differs partially from the original substance. Examples of such a variant include a substitution variant, an addition variant, a deletion variant, a truncated variant, an allelic variant, and the like. The term "allele" as used herein refers to a genetic variant located at a locus identical to a corresponding gene, where the two genes are distinguished from each other. Therefore, the term "allelic variant" as used herein refers to a variant which has an allele relationship with a certain gene. The term "homolog" of a nucleic acid molecule as used herein refers to a nucleic acid molecule having a nucleotide sequence having homology with the nucleotide sequence of a reference nucleic acid molecule. Representatively, "homolog" refers to a polynucleotide which hybridizes to a reference nucleic acid molecule under stringent conditions. In the case of the nucleic acid molecule of the present invention, a "homolog" is a nucleic acid molecule having a nucleic acid sequence having homology with a nucleic acid sequence encoding the amino acid sequence of a protein, whose biological function is the same as or similar to the promoter of the present invention. Therefore, the concepts of the terms "homolog" and "variant" overlap partially. Therefore, a homolog has amino acid or nucleotide homology with a certain gene in a certain species (preferably at least 60% homology, more preferably at least 80%, at least 85%, at least 90%, and at least 95% homology). A method for obtaining such a homolog is clearly understood from the description of the present specification.

When introduction of a virus construct into a cell is herein required, the virus construct may be introduced into a cell by any method for introducing DNA into a cell. Examples of such a method include transfection, transduction, transformation, and the like (e.g., electroporation, a method using a particle gun (gene gun), and the like).

Pharmaceutical (medicinal) compositions herein preferably contain the herpes virus of the present invention and a pharmaceutically acceptable carrier. Such pharmaceutical compositions are in any form as long as it is effective to a host. Examples of the form include, but are not limited to, powders, granules, capsules, tablets, caplets, pills, solutions, troches, buccal tablets, sublingual tablets, vaginal tablets, elixirs, syrups, lemonades, suspensions, emulsions, aerosols, injections, infusions, nebulae, liniment, ointments, plasters, lotions, suppositories, and the like. Preferably, the present invention is provided in the form of vaccine injections. The present invention may be in the form of sustained preparations. A DDS technique may be applied to the present invention.

Preferably, the pharmaceutical composition of the present invention contains at least $10^3$ herpes viruses, and preferably at least $2\times10^3$, at least $5\times10^3$, at least $10^4$, at least $2\times10^4$, at least $5\times10^4$, at least $10^5$, at least $2\times10^5$, at least $5\times10^5$, at least $10^6$, at least $2\times10^6$, at least $5\times10^6$, at least $10^7$, at least $2\times10^7$, at least $5\times10^7$, at least $10^8$, at least $2\times10^8$, at least $5\times10^8$, at least $10^9$, at least $2\times10^9$, at least $5\times10^9$, at least $10^{10}$, or at least more than $10^{10}$ herpes viruses. A suitable amount varies depending on circumstances. Those skilled in the art would determine the suitable amount, depending on the state of the active ingredient in a composition, or in the case of a medicinal composition, on the conditions of a patient, the conditions of a disease of a patient, the administration route, dosage form, or the conditions of a patient monitored during administration.

Examples of the pharmaceutically acceptable carrier include, but are not limited to excipients, binders, disintegrants, lubricants, antioxidants, preservatives, colorants, flavoring agents, stabilizers, coating agents, diluents, emulsifiers, suspending agents, solvents, fillers, bulky agents, buffers, delivery vehicles, and/or pharmaceutical adjuvants.

When the composition of the present invention is used as a pharmaceutical composition, the composition further contains the following medicinal ingredients:

central nerve system drugs (e.g., general anesthetics, sedative-hypnotics, anxiolytics, antiepileptics, anti-inflammatory agents, stimulants, antihypnotics, antiperkinson agents, antipycohtics, combination cold remedies, and the like);

peripheral nerve agents (e.g., local anesthetics, skeletal muscle relaxants, autonomic nerve agents, antispasmodic agents, and the like);

sensory organ drugs (e.g., ophthalmological agents, otorhinolaryngological agents, antidinics, and the like):

circulatory organ drugs (e.g., cardiotonics, antiarrhythmics, diuretics, antihypertensive agents, vasoconstrictors, vasodilators, antihyperlipemia agents, and the like);

respiratory organ drugs (e.g., respiratory stimulants, antitussives, expectorants, antitussive extpectorants, bronchodilators, collutoriums, and the like);

digestive organ drugs (e.g., stegnotics, antiflatuents, peptic ulcer agents, stomachics, antacids, cathartics, enemas, cholagogues, and the like);

hormone agents (e.g. pituitary gland hormone agents, salivary gland hormone agents, thyroid gland hormone agents, accessory thyroid gland hormone agents, anabolic steroid agents, adrenal gland hormone agents, androgenic hormone agents, estrogen agents, progesterone agents, mixed hormone agents, and the like);

urogenital organ and anus drugs (e.g., urinary organ agents, genital organs agents, uterotonics, hemorrhoids agents, and the like);

dermatologic drugs (e.g., dermatologic disinfectants, wound protecting agents, pyogenic diseases agents, analgesics, antipruritics, astringents, antiphlogistics, parasitic skin diseases agents, emollients, hair agents, and the like);

dental and oral agents;

drugs for other organs;

vitamin agents (e.g., vitamin A agents, vitamin D agents, vitamin B agents, vitamin C agents, vitamin E agents, vitamin K agents, mixed vitamin agents, and the like):

nutritive agents (e.g., calcium agents, inorganic preparations, saccharides agents, protein amino acid preparations, organ preparations, infant preparations, and the like);

blood and body fluid drugs (e.g., blood substitute agents, styptics, anticoagulants, and the like):

dialysis drugs (e.g., kidney dialysis agents, peritonea dialysis agents, and the like);

other metabolic drugs (e.g., organ disease agents, antidotes, antabuses, arthrifuges, enzyme preparation, diabetic agents, and others);

cell activating agents (e.g., chlorophyll preparations, pigment agents, and the like);

tumor agents (e.g., alkylation agents, antimetabolites, antineoplastic antibiotic preparations, antineoplastic plant extract preparations, and the like);

radiopharmaceuticals;

allergy drugs (e.g., antihistamic agents, irritation therapy agents, non-specific immunogen preparations, and other allergy drugs, crude drugs and drugs based on Chinese medicine, crude drugs, Chinese medicine preparation, and other preparations based on crude drug and Chinese medicine formulation);

antibiotic preparations (e.g., acting for gram-positive bacteria, gram-negative bacteria, gram-positive mycoplasmas, gram-negative mycoplasmas, gram-positive rickettsia, gram-negative rickettsia, acid-fast bacteria, molds, and the like);

chemotherapeutic agents (e.g., sulfa drugs, antitubercular agents, synthetic antimicrobial agents, antiviral agents, and the like);

biological preparations (e.g., vaccines, toxoids, antitoxins, leptospire antisera, blood preparations, biological test preparations, and other biological preparations, and antiprotozoal drugs, anthelmintics, and the like);

dispensing agents (e.g., excipients, ointment bases, solvents, flavors, colorants, and the like);

diagnostic drugs (e.g., contrast media, function testing reagents, and the like);

sanitation drugs (e.g., preservative):

xenodiagnostic drugs (e.g., cytologic examination drugs, and the like);

non-categorized drugs which do not aim mainly for therapy; and narcotics (e.g., opium alkaloid drugs, coca alkaloid preparations, synthetic narcotics, and the like).

The pharmaceutical composition of the present invention can be easily produced by those skilled in the art with reference to Japanese Pharmacopeia, United States Pharmacopoeia, Pharmacopoeias of other countries, Remington's Pharmaceutical Sciences, 18th Edition, A. R. Gennaro, ed., Mack Publishing Company, 1990, or the like.

When the present invention is prescribed as a pharmaceutical composition, it may be parenterally administered. Alternatively, such a composition may be intravenously or subcutaneously administered. When administered systemically, therapeutic compositions for use in the present invention maybe in the form of orally acceptable aqueous solution which does not contain a pyrogen. Such a pharmaceutically acceptable aqueous solution maybe prepared by techniques in the art if pH, isotonicity, stability, and the like are carefully controlled.

In a preferred embodiment, the HSV of the present invention or a pharmaceutical composition containing the same may be administered in the form of inoculation. The pharmaceutical composition containing the attenuated HSV of the present invention is not limited to a particular inoculation form and can be used in any known form. Preferably, such a composition is inoculated as an injection of aqueous solution or suspension to a patient. Such an injection includes infusion solution, supplements, and the like.

The above-described injection may contain a commonly used additive in addition to the attenuated HSV of the present invention. The additive is not particularly limited. For example, the injection may optionally contain a surfactant, an emulsifier, suspending agents, a preservative, a soothing agent, a stabilizer, or the like as an ingredient. Examples of the surfactant include Tween80, polyoxyl 40 stearate, sorbitan sesquioleate, glyceryl monostearate, lauromacrogol, and the like. Examples of the emulsifier include gum arabic, traganth, sodium alginate, and the like. Examples of the suspending agents include aluminum monostearate, carboxymethyl cellulose, methyl cellulose, and the like. Examples of the preservative include phenol, phenylmercuric nitrate, benzalkonium chloride, benzethonium chloride, benzyl alcohol, chlorobutanol, and the like. Examples of the soothing agent include benzyl alcohol, chlorobutanol, sorbitol, and the like. Examples of the stabilizer include buffering agents, such as citric acid, acetic acid, tartaric acid, succinic acid, and the like, propylene glycol, diethylin, sulfite, ascorbic acid, Rongalite, and the like.

Further, water, physiological saline, dextrose, glycerol, ethanol, propylene glycol, polyethylene glycol, vegetable oil, organic ester such as ethyl oleate and the like, pH buffering agents, adjuvant, immune activators for enhancing the effect of attenuated HSV, and the like may be added.

In the present invention, a method for producing the above-described injections are not particularly limited. The injections may be produced by a commonly used device and method. The prepared injections may be subjected to bacteria elimination by filtration, and optionally to lyophilization and the like. The injections are administered subcutaneously, intramuscularly, intravenously, intratumorally, intraperitoneally, intratracheally, intravesically, intraintestinally, intrarectally, intrabuccally, intraocularly, intraarterially, or the like by a commonly used method or by infusion.

The above-described injections may be dissolved into solution immediately before administration. The injections may be prepared in the form of a solid.

The accurate doses of individual pharmaceutical compositions containing the attenuated HSV of the present invention vary depending on an administration method, differences between individual subject patients, types of diseases, the conditions of subject patients, and are not necessarily determined in the same manner. However, for example, when administered to a human as an injection, the dose of attenuated HSV is about 0.01 ng to 10 mg/kg a day at one or several dosage times for an adult. Preferably, administration may be conducted while monitoring the conditions of a patient if necessary.

The attenuated HSV of the present invention can be used in conjunction with a prodrug in accordance with a known method. The administration route and dose of the prodrug are determined in accordance with the known method. The prodrug can be used simultaneously or alternately with the attenuated HSV of the present invention.

The present invention may also be administered preferably in the form of a vaccine. Vaccine means an antigen in any of various-forms (e.g., protein, DNA, and the like) which is used to prevent (or treat) a certain type of disease (e.g., contagious diseases, infectious diseases, and the like). Attenuated live pathogens (live vaccine), inactive pathogens (or a part thereof), metabolites of a pathogen (toxin, inactivated toxin (i.e., toxoid), or the like), DNA vaccines, or the like are used depending on the type of infection, transmission, epidemic, or the like. Vaccination actively develops immunity (humoral immunity, cell-mediated immunity, or both) within the body of organisms (humans, livestock, and vectors) and prevent the infection, transmission, epidemic, or the like of pathogens.

The vaccines of the present invention are not particularly limited to any dosage form, and are prepared in accordance with methods per se known in the art. The vaccines of the present invention are preferably live vaccines containing the above-described HSV gene recombinant. Further, the vaccines of the present invention may be in the form of an emulsion containing various adjuvants. The adjuvants aid sustenance of a high level of immunity when the above-described HSV gene recombinant is used in a smaller dose than when it is used alone. Examples of the adjuvants include Freund's adjuvant (complete or incomplete), adjuvant 65 (including peanut oil, mannide monooleate and aluminum monostearate), and aluminum hydrate, aluminum phosphate or mineral gel such as alum. For vaccines for humans-or edible animals, adjuvant 65 is preferable. For vaccines for commercial animals, mineral gel is preferable.

In addition to the above-described adjuvants, the vaccines of the present invention may contain at least one additive for preparations selected from diluents, aroma chemicals, preservatives, excipients, disintegrants, lubricants, binders, surfactants, plasticizers, and the like.

The administration routes of the vaccines of the present invention are not particularly limited. However, the vaccines are preferably administered parenterally (e.g., intravenously, intraarterially, subcutaneously, intradermal, intramuscularly or intraperitoneally).

The dose of the vaccines of the present invention can be selected depending on various conditions: whether administration is intended to prevent or treat diseases caused by HSV infection: whether infection is primary or recurrent: the age and weight, conditions of patients; the severity of disease; and the like. When intended to treat diseases caused by recurrent infection, the dose of the vaccines of the present invention can be preferably about 0.01 ng to 10 mg per kg weight, more preferably about 0.1 ng to 1 mg/kg.

The number of administrations of the vaccines of the present invention varies depending on the above-described various conditions, and is not necessarily determined in the same manner. However, preferably, the vaccines are repeatedly administered at the intervals of days or weeks. Particularly, administration is conducted at a total of several times, or preferably about one to two times, at the intervals of about 2 to 4 weeks. The number of administrations (administration time) is preferably determined by symptomatology or a fundamental test using antibody titer while monitoring the conditions of diseases.

The term "diseases or disorders" as used herein refers to diseases or disorders to which the virus constructs of the present invention are effective. Examples of the diseases or disorders include herpes virus-related diseases or disorders (e.g., gingivostomatitis, herpes facialis, herpes labialis, herpes keratoconjunctivitis, herpes encephalitis, genital herpes, neonatal herpes, chickenpox, herpes zoster, infectious mononucleosis, Burkitt's lymphoma, rhinopharyngeal cancer, pneumonia, cytomegalic inclusion disease, exanthema subitum, pneumonia, Kaposi's sarcoma, PEL, Castleman's disease), cancer (e.g., ovarian cancer, liver cancer, pancreatic cancer, bladder cancer, urethra cancer, colon cancer, skin cancer, malignant melanoma, osteosarcoma, head and neck squamous cell carcinoma, stomach cancer, prostate cancer, breast cancer, lung cancer, colon cancer, lymphoma, hepatoma, mesothelioma, melanoma, astrocytoma, oligodendroglioma, meningioma, neurofibroma, glioblastoma, ependymoma, schwannoma, neurofibrosarcoma, medulloblastoma, fibrosarcoma, squamous cell carcinoma, neuroectoderm cancer, thyrocele, pituitary gland tumor, epidermoid carcinoma, and the like), other diseases or disorders (e.g., diseases or disorders caused by other viruses (e.g., HIV, influenza virus, rotavirus, and the like) or bacteria (e.g., *Bordetella pertussis, Corynebacterium diphtheriae, Clostridium tetani*, and the like)), prokaryotes (e.g., gonococcus, *Listeria monocytogenes*, dysentery *bacillus*, and the like) and eukaryotes (e.g., unicellular pathogens, multicellular parasites, and the like).

Therefore, the herpes simplex virus of the present invention and a composition containing the same can be used to prevent or treat cancer as described above. Preferably, the herpes simplex virus of the present invention and a composition containing the same may be applied to progressive pancreatic cancer, ovarian cancer, and the like which usually occur with peritoneal dissemination and are difficult to treat by surgical excision or chemotherapy, and to solid tumor. The present invention may be used to immunize an individual against at least one form of cancer. Particularly, the present invention may be used to precautiously immunize a human individual having a disposition to suffer from a particular cancer or a human individual who has previously had cancer and therefore has the risk of recurrence. The development of genetics, technology and epidemiology makes it possible to determine the possibility and risk assessment of the occurrence of cancer for individuals. With gene screening and/or a family health history, it is possible to predict the possibility of the occurrence of any of several types of cancers for individuals.

Pharmaceutical compositions containing the attenuated HSV of the present invention may be prepared by combining an effective amount of the attenuated HSV with an appropriate medicinal carrier and other additives by a commonly used method. "Effective amount" refers to the amount necessary or sufficient to exhibit an intended effect with little side effect, although it varies depending on the type or usage form thereof and is not necessarily determined in the same manner.

The pharmaceutical compositions containing the attenuated HSV of the present invention can be inoculated to patients in known forms, preferably injections of aqueous solution or suspension. The inoculation forms are not particularly limited. The injections include infusion solution, nutritive replenishing solution, and the like.

The injections may contain a commonly used additive in addition to the attenuated HSV of the present invention. Examples of the additive include, but are not particularly limited to, surfactants, emulsifiers, suspending agents, preservatives, soothing agents, stabilizers, and the like, which are optionally used. Examples of the surfactants include Tween80, polyoxyl 40 stearate, sorbitan sesquioleate, glyceryl monostearate, lauromacrogol, and the like. Examples of the emulsifiers include gum arabic, traganth, sodium alginate, and the like. Examples of the suspending agents include aluminum monostearate, carboxymethyl cellulose, methyl cellulose, and the like. Examples of the preservatives include phenol, phenylmercuric nitrate, benzalkonium chloride, benzethonium chloride, benzyl alcohol, chlorobutanol, and the like. Examples of the soothing agents include benzyl alcohol, chlorobutanol, sorbitol, and the like. Examples of the stabilizers include buffering agents (e.g., citric acid, acetic acid, tartaric acid, succinic acid, and the like), propylene glycol, diethylin, sulfite, ascorbic acid, Rongalite, and the like.

Further, water, physiological saline, dextrose, glycerol, ethanol, propylene glycol, polyethylene glycol, vegetable oil, organic ester such as ethyl oleate and the like, pH buffering agents, adjuvants, immune activators for enhancing the effect of attenuated HSV, and the like may be added.

In the present invention, a method for producing the above-described injections are not particularly limited. The injections may be produced by a commonly used device and method. The prepared injections may be subjected to bacteria elimination by filtration, and optionally to lyophilization and the like. The injections are administered subcutaneously, intramuscularly, intravenously, intratumorally, intraperitoneally, intratracheally, intravesically, intraintestinally, intrarectally, intrabuccally, intraocularly, intraarterially, or the like by a commonly used method or by infusion.

The above-described injections maybe dissolved into solution immediately before administration. The injections may be prepared in the form of a solid.

The accurate doses of individual pharmaceutical compositions containing the attenuated HSV of the present invention vary depending on an administration method, differences between individual subject patients, types of diseases, the conditions of subject patients, and are not necessarily determined in the same manner. However, for example, when administered to a human as an injection, the dose of attenuated HSV is about 0.01 ng to 10 mg/kg a day at one or several dosage times for an adult. Preferably, administration may be conducted while monitoring the conditions of a patient if necessary.

The attenuated HSV of the present invention can be used in conjunction with a prodrug in accordance with a known method. The administration route and dose of the prodrug are determined in accordance with the known method. The prodrug can be used simultaneously or alternately with the attenuated HSV of the present invention.

The term "prodrug" as used herein refers to a drug which is inactive as it is and becomes active when it is chemically changed in the body by a drug-metabolizing enzyme (e.g., purine and pyrimidine derivatives used as chemotherapeutic agents for cancer). Examples of the prodrugs herein preferably include ganciclovir, acyclovir, taxol, camptothecin, guanine nucleoside derivatives (e.g., A-5021), and the like. A prodrug herein preferable for the present invention is a prodrug which is converted to an active form by a suicide gene contained in the attenuated HSV of the present invention.

The term "suicide gene" as used herein refers to a gene which can kill the cell in which it is expressed. Representatively, such a gene is a metabolically toxic gene. For example, a method for introducing a suicide gene incorporated into a virus construct into tumor cells to drive them to suicide is herein exemplified. Specifically, thymidine kinase may be transduced into herpes simplex virus.

The term "ability to select cancer cells" as used herein indicates that the growth rate in cancer cells is higher than in normal cells.

The present invention may be provided in conjunction with an immunomodulatory protein. The term "immunomodulatory protein" as used herein refers to proteins and nucleic acid molecule expression products which accelerate and/or regulate immune responses. Therefore, in a preferred embodiment, the immunomodulatory proteins may be delivered as an immunotherapeutic agent, or an ingredient of a vaccine.

Examples of the immunomodulatory proteins include chemokines, adhesive molecules, cytokines, co-stimulatory molecule, growth factors, and receptor molecules. The chemokines include MIP-1$\alpha$, MIP-1$\beta$, RANTEs, IL-8 and MCP-1. Examples of the adhesive molecules include selectin family constructs, mucin-like molecules, integrin family constructs, and immunoglobulin superfamily constructs. Examples of the select in family constructs include L-selectin, P-selectin, and E-selectin. The mucin-like molecules are ligands for the selectin family constructs. Examples of the mucin-like molecule include CD34, GlyCAM-1, and MadCAM-1. Examples of the integrin family constructs include LFA-1, VLA-1, Mac-1, and p150.95. Examples pf the immunoglobulin superfamily constructs include PECAM-1, ICAMs (ICAM-1, ICAM-2, and ICAM-3), CD2, and LFA-3. Examples of the cytokine include mutants of M-CSF, GM-CSF, G-CSF, CSF, IL-4, and IL-18 (including deletion of the first about 35 amino acid residues residues which are present in the precursor of a protein but are not present in the protein in the mature form). Examples of co-stimulatory molecules include CD40 and CD40 ligands (CD40L). Examples of growth factors include IL-7, nerve growth factors, and a vascular endothelial growth factor. Examples of the receptor molecules include a Fas lethal gene expression product, a tumor necrosis factor TNF receptor, Flt, Apo-1, p55, WSL-1, DR3, TRAMP, Apo-3, AIR, LARD, NGRF, DR4, DR5, KILLER, TRAIL-R2, TRICK2, and DR6. The compositions of the present invention may contain caspase (ICE).

In one embodiment of the present invention, the immunomodulatory proteins are delivered by administrating the nucleic acid molecules which are expressed into the immunomodulatory proteins when taken into cells. In some embodiments of the present invention, the immunomodulatory proteins are delivered by administrating the proteins per se. In some embodiments of the present invention, the immunomodulatory proteins are delivered by administrating the nucleic acids or the proteins per se. In one embodiment of the present invention, the immunomodulatory proteins are delivered by administrating the nucleic acids and the proteins per se simultaneously.

In some embodiments of the present invention, the above-described immunomodulatory proteins (as proteins or nucleic acid molecules encoding the proteins) are administered as a supplement along with a composition or otherwise a vaccine composition. In this case, the vaccine is any of a subunit, an inactivated vaccine, an attenuated live vaccine, a cellular vaccine, a recombinant vaccine, and a nucleic acid or DNA vaccine. In the case of the attenuated live vaccine, the cellular vaccine, the recombinant vaccine, or the nucleic acid or DNA vaccine, the immunomodulatory proteins are encoded by the nucleic acid molecules of the vaccines.

Compositions (e.g., vaccine) are herein provided for treating or preventing pathogens other than herpes virus (e.g., viruses (e.g., HIV, influenza virus, rotavirus, and the like), or bacteria). Such compositions comprise at least one gene of the pathogen which is included in an attenuated herpes virus as an exogenous gene. The exogenous gene preferably is full length but may be a partial sequence as long as it contains at least an epitope capable of triggering immunity. The term "epitope" as used herein refers to an antigenic determinant whose structure has been revealed. A method for determining an epitope is known in the art. Once the primary nucleic acid or amino acid sequence of a protein is provided, such epitopes can be determined by such a known routine technique. A useful epitope may have at least a length of three amino acids, preferably, at least 4 amino acids, 5 amino acids, 6 amino acids, 7 amino acids, 8 amino acids, 9 amino acids, 10 amino acids, 15 amino acids, 20 amino acids, or 25 amino acids.

Examples of such an exogenous gene include, but are not limited to, gp120, gp41 and gp17 matrix proteins, p24 capsid protein, reverse transcriptase (HIV pol), tat rev, and the like in the case of HIV; VP4, VP6 and VP7 and the like in the case of rotavirus, and HA, NA and NP and the like in the case of influenza virus.

The immunomodulatory proteins are useful in inducing and accelerating cytotoxic T lymphocyte (CTL) responses and/or antibody responses, and/or T lymphocyte growth responses.

The immunomodulatory proteins which induce and accelerate CTL responses are particularly useful when administered in conjunction with or as a part of vaccines against pathogens inside cells, autoimmune diseases, or cancers. The immunomodulatory protein which induce and accelerate CTL responses are particularly useful when administered along with attenuated live vaccines, cellular vaccines, recombinant vaccines, and nucleic acid or DNA vaccines. Alternatively, the immunomodulatory protein which induce and accelerate CTL responses are useful as an immunotherapeutic agent which is administered for patients with cancer or intracellular infection. The immunomodulatory protein which induce and accelerate CTL responses are useful when administered to immunocompromised patients.

Subject hosts of diseases may be herein any animal which can be injected with herpes virus. Examples of such animals include primates (e.g., monkeys and humans), cattles (e.g., beef cattle and dairy cattle), horses, pigs, cats, dogs, chickens, and the like. The hosts are preferably primates, and more preferably humans.

The age of subject hosts may be herein any age at which the subject hosts can be infected with herpes virus. For example, the subject hosts include the elderly, adults, children, babies, fetuses, and the like.

BEST MODE FOR CARRYING OUT THE INVENTION

The present invention provides herpes virus in which a non-essential gene for replication is inactivated. More specifically, the present invention provides herpes virus in which a non-essential gene for replication present in the UL or US region is inactivated. Conventionally, herpes virus in which a gene in an inverted repeat region is modified to transform its characteristic is used. However, it cannot be said that there is a herpes virus which is clinically effective to diseases caused by herpes virus or cancer. Therefore, by inactivating a non-essential gene for replication in the UL or US region, desired characteristics (e.g., attenuation, selectivity to cancer cells, an increase in safety for hosts (e.g., humans), and the like) can be obtained, resulting in utility advantageous over conventional techniques.

In one embodiment, the vaccines of the present invention are characterized by containing a HSV gene recombinant which does not express US3. Examples of such a recombinant include a gene recombinant in which among the HSV genes, the US3 gene is treated so as not to be translated; a gene recombinant in which among the HSV genes, the US3 gene is subjected to recombination, and when the recombined gene is translated, a protein different from US3 is expressed; and the like.

A gene recombination process for preparing the above-described gene recombinant is not particularly limited. For example, a part or entirety of the US3 gene is deleted; a part or entirety of the US3 gene is substituted; a part of the US3 gene is inverted, a part of the US3 gene is repeated; a part of the US3 gene is translocated; a gene fragment is inserted in the US3 gene so as to interrupt the US3 gene; and the like. Among them, deleting a part or entirety of the US3 gene, substituting a part or entirety of the US3 gene, or inserting a gene fragment in the US3 gene so as to interrupt the US3 gene is preferable. Particularly, inserting a gene fragment in the US3 gene so as to interrupt the US3 gene is more preferable. Even more preferably, the gene fragment to be inserted contains a signal which stops translation. As a signal which stops translation, a polyadenylation signal derived from SV40 is preferable.

The above-described gene recombination process is well established in the art and therefore can be easily conducted in accordance with, for example, a commercially available experimental manual, e.g., Molecular Cloning (Cold Spring Harbor Laboratory), issued in 1982; Molecular Cloning, 2nd ed. (Cold Spring Harbor Laboratory), issued in 1989; or the like.

Figure 10:
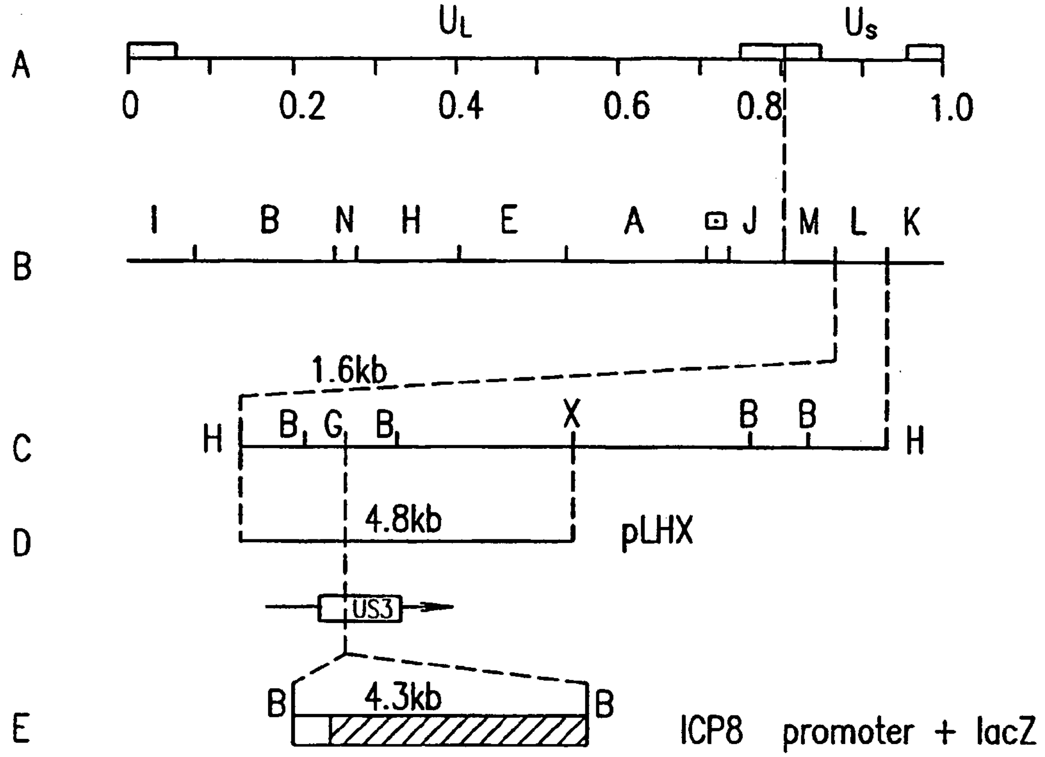
FIG. 10A is a schematic diagram showing a gene of HSV-2. This schematic diagram is accompanied by a map unit.
FIG. 10B is a cleavage map of HVS-2 strain 186 by Hind III.
FIG. 10C shows the corresponding positions of restriction enzyme (restriction endonuclease cleavage site) on the map, which relate to the present invention. It should be noted that in the figure, H indicates restriction enzyme sites of Hind III, B indicates restriction enzyme sites of Bam HI, G indates restriction enzyme sites of Bal II, X indicates restriction enzyme sites of Xba I.
FIG. 10D indicates the position of the US3 gene in a 4.8-kb Hind III-Xba I fragment precloned by pLHX which is pBluescript.
FIG. 10E shows a 4.3-kb Bam HI fragment containing a gene encoding lazZ fused with a HSV-1 β8 promoter and a polyadenylation signal derived from SV40 at 5' end and 3' end, respectively. The 4.3-kb Bam HI fragment was inserted into restriction enzyme sites of pLHX by Bal II, thereby preparing a gene recombinant pHZL1.

The "HSV gene recombinant which does not express US3" used in the present invention includes L1BR1. L1BR1 is prepared using HSV-2 strain 186. This preparation method will be described below with reference to FIG. 10.

FIG. 10A shows the gene of the HSV-2 strain 186, indicating the map units. FIG. 10B shows a Hind III cleavage map of the strains. As can be seen from FIGS. 10C and 10D, the US3 gene is present in a Hind III L fragment of 9.6 kb which is the US region (FIG. 10B). According to the base information of the US region, the Bgl II cleavage site in the 9.6-kb Hind III L fragment (G in FIG. 10C) is contained in the US3 gene (FIGS. 10C and 10D). Therefore, with the Bgl II cleavage site, the US3 gene is inactivated, thereby preparing a US3-deficient HSV.

It should be noted that it is known that the restriction endonuclease cleavage pattern (FIG. 10C) of the HSV-2 strain 186 by Bam HI, Xba I, Bal II matches that. of a HSV-2 strain HG52 (McGeoch et al., 1987).

More specifically, a 4.8-kb Hind III-Xba I fragment is preliminarily cloned from the gene of the HSV-2 strain 186. A method for preliminary cloning maybe conducted using a known cloning vector like pBluescript such as pLHX and the like in accordance with a method per se known.

Thereafter, the above-described preliminarily cloned Hind III-Xba I fragment is digested with Bgl II, so that a reading frame of 1443 bp is cleaved at a 215th residue from the 5' end. A 4.3-kb gene fragment shown in FIG. 10E is inserted into the cleavage site. Specifically, the gene fragment shown in FIG. 10E is a 4.3-kb Bam HI fragment containing a gene encoding lacZ fused with a HSV-1 β8 promoter at the 5' end and a polyadenylation signal derived from SV40 at the 3' end. The polyadenylation signal derived from SV40 stops the translation of the lacZ gene (Spaete and Mocarski, 1985; and Ho and Mocarski, 1988).

The resultant gene having the US3 gene interrupted by the lacZ gene, i.e., a gene in which a gene fragment indicated by E at position "G" in the gene fragment shown in FIG. 10C, is cloned by a known method. It should be noted that a gene recombinant obtained by inserting the above-described gene into a known cloning vector pLHX is referred to as pHZL1.

Thereafter, Vero cells are cotransfected with the complete DNA of the infectious HSV-2 strain 186 and the DNA of the linear pHZL1 containing the US3 gene interrupted by the lacZ gene (simultaneous introduction into cells). The two simultaneously introduced genes are recombined, the HSV gene recombinant is multiplied in the Vero cells. The HSV gene recombinant containing the US3 gene interrupted by the lacZ gene can be selected by the colors of plaques stained by Xgal staining. Specifically, since the lacZ gene encodes β-galactosidase, if the HSV gene recombinant contains the lacZ gene, β-galactosidase is expressed. This enzyme reacts with its substrate Xgal (5-bromo-4-chloro-3-indolyl-β-D-galactopyranoside) to produce a dark blue degradation products. Therefore, by selecting blue plaques, the HSV gene recombinant containing the lacZ gene can be selected. One of the selected gene recombinants is purified by the selection of a blue plaque, followed by further five rounds of plaque cloning. The purified gene recombinant is grown in Vero cells to prepare L1BR1.

Whether or not the above-described gene recombinant L1BR1 contains the lacZ gene at a site which interrupts the US3 gene can be determined by comparing L1BR1 with the gene of a wild-type HSV-2 strain 186. Specifically, the L1BR1 gene is treated with a restriction enzyme, followed by Southern blotting hybridization analysis using a 1.6-kb Bam HI fragment in the Hind III L fragment as a probe. The gene of the wild-type HSV-2 strain 186 is treated in the same manner. As a result, if the 1.6-kb fragment which is observed in the wild-type gene is lost in the L1BR1 gene, it can be confirmed that the lacZ gene interrupts the US3 gene.

Preferably, the attenuated HSV of the present invention has ability to select cancer cells, i.e., can be multiplied favorably in cancer cells.

In another embodiment, as an attenuated HSV in which at least one accessory gene is inactivated, UL39 or UL40 maybe in activated. Particularly, an attenuated HSV in which UL39 or UL40, and at least one other accessory gene are inactivated is preferable.

The attenuated HSV in which UL39 or UL40 is inactivated must rely on a host for ribonucleotide reductase which is encoded by UL39, and UL40 and is necessary for DNA and deoxyribonucleotide metabolism. Therefore, when the attenuated HSV in which UL39 or UL40 is inactivated is inoculated into cancer patients, the attenuated HSV can be multiplied favorably in actively dividing cancer cells. The cancer cells infected with the attenuated HSV are preventing from growing due to the cytopathic effect of the virus, potentially leading to death.

When at least one other accessory gene is inactivated in addition to UL39 or UL40, the pathogenicity of the attenuated HSV can be further reduced while maintaining the favored growth in cancer cells.

Examples of the attenuated HSV in which UL39 or UL40 and at least one other accessory gene are inactivated include an attenuated HSV in which UL39 (or UL40), UL55 and UL56 are inactivated, an attenuated HSV in which UL39 (or UL40) and UL2 are inactivated, an attenuated HSV in which UL39 (or UL40) and US3 are inactivated, an attenuated HSV in which UL39 (or UL40), UL2 and US3 are inactivated, and the like.

The attenuated HSV in which UL39 (or UL40), UL55 and UL56 are inactivated and the attenuated HSV in which UL39 (or UL40) and UL2 are inactivated have a higher level of safety than that of the attenuated HSV in which only UL39 (or UL40) is inactivated. The attenuated HSV in which UL39 (or UL40) and US3 are inactivated and the attenuated HSV in which UL39 (or UL40), UL2 and US3 are inactivated can cause apoptosis in a cancer cell as well as having a high level of ability to select cancer cells.

The vaccines of the present invention are useful as an agent for preventing and treating the above-described diseases caused by HSV. Particularly, the vaccines of the present invention are useful for an agent for preventing and treating sexually transmitted diseases (e.g., genital herpes) caused by HSV.

By administration of the vaccines of the present invention, the severity and/or infection rate of HSV infection can be reduced.

As can be seen from the Examples described below, a US3-deficient HSV gene recombinant contained in the vaccines of the present invention increases the number of $Fas^+$ mononuclear cells, and quickly activates dendritic cells, macrophages, and T cells. Further, the recombinant increases IL-12 which is an antiviral cytokine, and IFN-γ (interferon γ). IL-12 and IFN-γ stimulate and activate TH1 cells which in turn activate cell-mediated immunity. Thus, by administration of the vaccines of the present invention containing the US3-deficient HSV gene recombinant, an immune function against HSV infection is activated, so that the severity and/or infection rate of HSV infection can be reduced as described above.

Recently, it is indicated that the US3 gene of herpes simplex virus type 1 (hereinafter referred to as HSV-1) and HSV-2 is necessary for inhibition of apoptosis in infected cells (Leopardi, R., Van Sant, and Roizman B. (1997), Proc. Natl. Acad. Sci. USA. 94, 7891-7896; Asano, S., Honda, T., Goshima, F., Watanabe, D., Miyake, Y., Sugiura, Y., and Nishiyama, Y. (1999), J. Gen. Virol. 80, 51-56). Therefore, the US3-deficient HSV gene recombinant has an advantage of lacking inhibition of apoptosis in infected cells. Specifically, when the US3-deficient HSV gene recombinant is administered, infected cells are immediately driven to apoptosis, so that the US3-deficient HSV gene recombinant is suppressed from being excessively multiplied. Moreover, the infected cells which has caused apoptosis play a role in antigen presentation, thereby further enhancing activation of immunity against HSV infection.

In another embodiment, in the attenuated herpes simplex virus of the present invention (hereinafter also referred to as attenuated HSV), out of non-essential genes for replication, the US3 gene, and/or the UL56 gene, which is a pathogenicity-related gene, are inactivated by deleting a part or entirety of the DNA base sequences thereof, or by base sequence substitutions, modifications, insertions, or the like. Alternatively, inactivation can be carried out by controlling transcription of the US3 gene and/or the UL56 gene.

One attenuated HSV used in the present invention is clone 10 (MNO10) which is one of clones collected from strain HF. This clone has the genome of herpes virus in which 3832 bps are deleted at positions 116515 to 120346, and 136 amino acids at the N terminus side out of a total of 197 amino acids of UL56, and its upstream region are deleted. MNO10 is preserved and distributed by the Laboratory of Virology, Research Institute for Disease Mechanism and Control, Nagoya University School of Medicine in accordance with the requirements under the Japanese Patent Law and is easily available.

The attenuated HSV of the present invention may be prepared using HSV-1 or alternatively HSV-2.

Examples of a method for inactivating the US3 and/or UL56 genes of the attenuated HSV include, but are not limited to, insertion of another sequence, removal of a part of a sequence, modification of a base, substitution of a base, and the like, which are known methods.

By inactivating the US3 gene and/or the UL56 gene, the attenuated HSV of the present invention can be multiplied favorably in cancer cells. Further, a suicide gene can be effectively expressed in targeted cancer cells, potentially leading to an effective anticancer function.

The attenuated herpes simplex virus of the present invention in which the US3 gene and/or the UL56 gene are inactivated is combined with a prodrug which is converted to an active form by the herpes virus, or is used alone without such a combination, to treat cancer.

In one preferred embodiment, the attenuated HSV of the present invention contains the thymidine kinase gene. In this case, if ganciclovir which is a prodrug is administered, the ganciclovir is converted to an active form by phosphorylation by thymidine kinase, thereby inhibiting DNA polymerase in cancer cells. Further, the attenuated HSV is taken into DNA, thereby inhibiting DNA and deoxyribonucleotide metabolism and DNA-independent RNA synthesis. A gene having such a function is called suicide gene. In the present invention, an exogenous suicide gene may be expressibly incorporated in addition to the above-described thymidine kinase gene.

The above-described exogenous suicide gene is, but not particularly limited to, any gene that can convert a prodrug to an active form. Examples of the exogenous suicide gene include a cytosine deaminase gene, the gpt gene of *E. coli*, the deoD gene of *E. coli*, a carboxyesterase gene, and the like.

In another preferred embodiment, the present invention provides a US3-deficient HSV-2 virus.

The present invention provides an improved method for immunizing an individual comprising the step of delivering a gene construct to cells in the individual as a part of a vaccine composition (including DNA vaccines, attenuated live vaccines, and recombinant vaccines). The gene construct comprises a nucleotide sequence which encodes an immunomodulatory protein and is operatively linked to a control sequence which can function in the vaccine so as to achieve expression of the gene construct. The improved vaccine causes an enhanced cell-mediated immune response.

The attenuated herpes simplex virus of the present invention in which the US3 gene and/or the UL56 gene are inactivated is combined with a prodrug which is converted to an active form by the herpes virus, or is used alone without such a combination, to treat cancer.

Examples of the prodrugs herein preferably include ganciclovir, acyclovir, taxol, camptothecin, and the like. A prodrug herein preferable for the present invention is a prodrug which is converted to an active form by a suicide gene contained in the attenuated HSV of the present invention.

The attenuated HSV of the present invention contains the thymidine kinase gene. In this case, if ganciclovir which is a prodrug is administered, the ganciclovir is converted to an active form by phosphorylation by thymidine kinase, thereby inhibiting DNA polymerase in cancer cells. Further, the attenuated HSV is taken into DNA, thereby inhibiting DNA and deoxyribonucleotide metabolism and DNA-independent RNA synthesis. A gene having such a function is called suicide gene. In the present invention, an exogenous suicide gene may be expressibly incorporated in addition to the above-described thymidine kinase gene.

The above-described exogenous suicide gene is, but not particularly limited to, any gene that can convert a prodrug to an active form. Examples of the exogenous suicide gene include a cytosine deaminase gene, the gpt gene of *E. coli*, the deoD gene of *E. coli*, a carboxyesterase gene, and the like.

EXAMPLE

Hereinafter, the present invention will be described by way of examples. The following examples are provided only for illustration purposes. Therefore, the present invention is not limited to the examples. The scope of the present invention is limited only by the appended claims. It should be noted that % indicates % by weight unless otherwise mentioned.

Example 1

Preparation of Attenuated HSV (UL39-inactivated HSV)

A DNA fragment of HSV-1 containing the UL39 gene was incorporated into plasmid pBluescript (manufactured by Stratagene) for cloning, so as to prepare DNA having a lacZ cassette interrupting the open reading frame of the UL39 gene. In this case, the lacZ cassette is a DNA fragment containing a promoter for the HSV UL39 at the 5' end thereof and the lacZ gene of *E. coli* and the polyadenylation signal of SV40 downstream of the promoter. Infectious HSV DNA was prepared from cells infected with HSV. Cells were transfected with this DNA. After three days, the produced viruses were collected. A plaque which was stained blue in the presence of X-gal was collected. Further plaque cloning was conducted three times. The resultant viruses were multiplied in Vero cells and then stocked. The thus-obtained mutant was subjected to Southern blot, PCR, Western blot, and the like, so that it was confirmed that UL39 was inactivated.

Example 2

Preparation of Attenuated HSV (Hh) in which UL39 and UL56 Genes not Involved in DNA and Deoxyribonucleotide Metabolism are Inactivated There is provided a strain HF derived from HSV-1 in which a region containing the UL56 gene is deficient (kindly provided by Dr. Shin Isomura, Department of Pediatrics, Nagoya University School of Medicine). The pathogenicity of this strain is significantly low when inoculated intraperitoneally in a mouse as compared to a wild type of the strain. Further, the strain causes cell fusion with infected cells. Vero cells were infected with the above-described UL39-deficient virus and the strain HF. Among the progeny viruses, viruses which cause cell fusion and produce blue plaque in the presence of X-gal were collected. After cloning the viruses, it was confirmed by PCR and Western blot that UL39 and UL56 are deficient in the viruses.

Example 3

Preparation of Strain in which Carboxyesterase is Incorporated into UL39-inactivated HSV A human carboxyesterase gene having a promoter for the immediate early gene of human cytomegalovirus was inserted to a lacZ gene (open reading frame) so that DNA in which the lacZ gene was interrupted by the human carboxyesterase gene was prepared. Vero cells were transfected with this DNA and infectious DNA derived from UL39-inactivated virus which has lacZ. Produced viruses were collected. Viruses which produced colorless plaques in the presence of X-gal were collected, followed by plaque cloning. The result antiviruses were stored as a primary stock. Cell samples were infected with clones obtained as the primary stock. The cell samples were subjected to a fluorescent antibody technique using tagged antibodies. For positive clones, a secondary stock was prepared. The finally obtained clones were confirmed to induce carboxyesterase activity in infected cells.

Example 4

Isolation of UL56-inactivated HSV-1

HSV-1 virus in which a region including the UL56 gene is deficient was isolated from strain HF. This HSV-1, HF-derived clone 10 (MNO10: preserved in the Laboratory of Virology, Research Institute for Disease Mechanism and Control, Nagoya University School of Medicine) was subjected to PCR, base sequence determination, and Western blot analysis to confirm that the UL56 gene is deficient.

Example 5

Preparation of Attenuated HSV (HR522) Capable of Forming a Giant Polynuclear Cell Vero cells (RIKEN Cell Bank, Tsukuba Science City, 305 Ibaraki, Japan) were infected with the UL39-attenuated HSV prepared in Example 1 and the HF-derived clone 10 of HSV-1 isolated in Example 4 in which the region including the UL56 gene is deficient. Thereafter, a clone which was capable both of producing a blue plaque in the presence of X-gal (marker for UL39-attenuated HSV) and producing a giant polynuclear cell (marker for HF MNO10) was selected. For confirmation, such a clone was separated by means of phenotype thereof. Those expressing LacZ (i.e., RR-), and having a feature of producing multinucleated giant cell in the infected cells. The clone obtained from this mixed infection is designated as HR522.

Example 6

Treatment of Cancer Using Attenuated HSV

SW1990 derived from human ovarian cancer was transplanted into groups of nude mice (female, 6 weeks old, each group includes 10 mice) by intraperitoneally injecting $1\times10^7$ cells/mouse in the vicinity of the pancreas under ether anesthesia. After the transplantation, $1\times10^7$ PFU/mouse of the UL39-inactivated HSV or HR522 was intraperitoneally injected into two groups on day 7 and day 12. After the inoculation of the UL39-inactivated HSV or HR522, ganciclovir of 0.4 mg/mouse was administered to one of each of the UL39-inactivated HSV and HR522 inoculation groups on day 10 (i.e., day 17 and 22 after the transplantation). The survival rate of each group was observed until day 60 after the transplantation. The results are shown in FIG. 1.

As can be seen from the result of FIG. 1, it was revealed that the survival time of nude mice is elongated by the inoculation of the UL39-inactivated HSV or HR522. Further, it was also revealed that the administration of ganciclovir further elongates the survival time. Particularly, the group given a combination of the HR522 inoculation and the ganciclovir administration had a high survival rate.

Example 7

Comparison of Attenuated HSV with Known Anticancer Agents

SW1990 derived from human ovarian cancer was transplanted into groups of nude mice (female, 6 weeks old, each group includes 10 mice) by intraperitoneally injecting $1\times10^7$ cells/mouse in the vicinity of the pancreas under ether anesthesia. After the transplantation, $5\times10^7$ PFU/mouse of the UL39-inactivated HSV or HR522, or taxol (known anticancer agent) of 0.4 mg/mouse was intraperitoneally injected into the respective group on day 7 and day 12. The survival rate of each group was observed until day 60 after the transplantation. The results are shown in FIG. 2.

Figure 2:
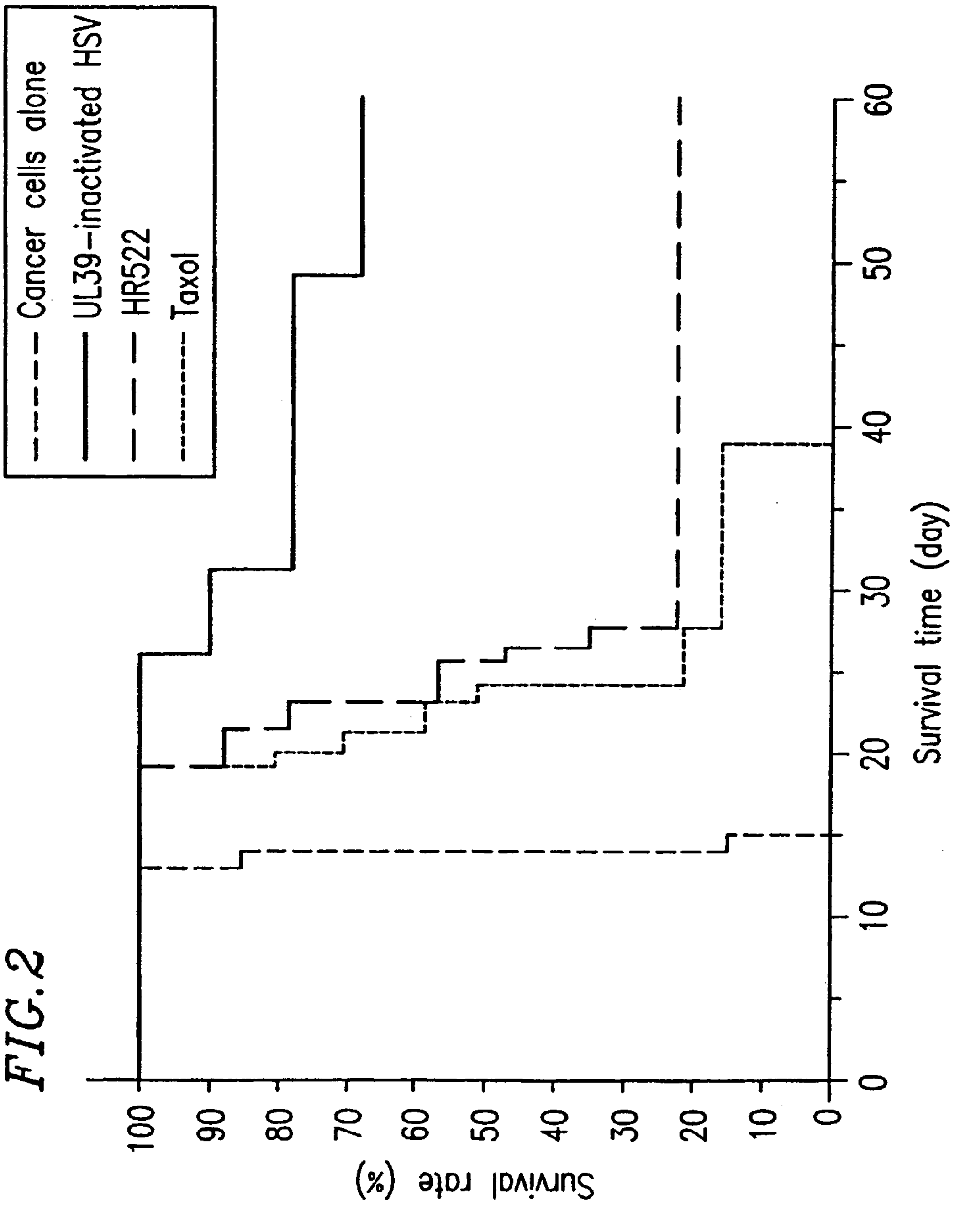
FIG. 2 is a graph showing comparison of a cancer treating effect between the attenuated HSV of the present invention and known anticancer agents.

As can be seen from the results shown in FIG. 2, it was revealed that the groups to which the UL39-inactivated HSV or HR522 was inoculated have a longer survival time than that of the group to which taxol was administered.

Example 8

Preparation of US3-deficient Virus (Mice and Virus)

Female BALB/c mice, 8 to 10 weeks old at the start of treatment, were purchased from Japan SLC (Hamamatsu, Japan). All of the mice were caged and maintained in accordance with institutionally recommended guidelines. A gene recombinant of HSV-2 strain 186 which does not have US3 (hereinafter referred to as L1BR1) was prepared by a method described in "Daikoku, T., Yamashita, Y., Tsurumi, T., Maeno, K., and Nishiyama, Y. (1993), Virology 197, 685-694". As a comparative example, wild-type HSV-2 strain 186 (hereinafter simply referred to as wild type 186) and strain YY2 which is a US2-deficient mutant were used. These three viruses were grown in Vero cells and then stored at −80° C. until use. Viral infection titers were measured using the Vero cells and were represented as plaque forming unit (PFU)/ml.

(HSV Infection Method)

Mice were inoculated intravaginally with the virses by a method described in "Parr, M. B., Kepple, L., McDermott, M. R., Drew, M. D., Bozzola, J. J., and Parr, E. R. (1994), Lab. Invest. 70,369-380", and "Milligan, G. N., and Bernstein, D. I. (1997), Virol. 229, 259-268". To synchronize the estrous cycle at the progesterone-dominated stage prior to viral inoculation, the mice were injected subcutaneously with 0.1 μg/mouse of β-estradiol 17-cypionate (hereinafter abbreviated as E) (Sigma, St. Louis, Mo.) with a treatment of 2 mg/mouse of Depo-Provera (hereinafter abbreviated as DP) (Sigma). Five days after the administration of DP, the mice were swabbed with gauze soaked in sodium pentbarbital to anesthetize the mice. The mice were intravaginally infected with 20 μl of a suspension of wild type 186, wild type YY2, or L1BR1.

(Viral Titration)

PBS (phosphate buffered saline) was placed on the vagina using a pipette to cause vaginal ravage. Thereafter, the vagina was stored at −80° C. in accordance with a method described in "Milligan, G. N., and Bernstein, D. I. (1997), Virol. 229, 259-268", until measurement of infection titer by plaque formation on a monomolecular layer of Vero cells.

(Preparation of Cells in Vagina)

Mononuclear cells (MNC) and epithelial cells (EC) derived from the vagina were obtained in accordance with a method described in "Inagaki-Ohara, K., Nishimura, H., Sakai, T., Lynch, D. H., andyoshikai, Y. (1997), Lab. Invest. 77, 421-429" which is modified from "Rakasz, E., Hagen M., Sandor, M., and Lynch, R.G. (1997), Int. immunol.9, 161-167". Briefly, the mice were lethally anesthetized and thereafter the vaginas were-excised from the mice. The vaginas were cut into 2 mm-size sections, followed by incubation in Hank's balanced salt solution containing 4 U/ml DNase I at 37° C. for 60 minutes. After shaking, the cell suspensions were passed through nylon wool columns to remove necrotized tissue sections, so that suspensions of single cells were obtained. The passed cells were centrifuged through a 40%/75% or 25%/40% discontinuous Percoll (Pharmacia, Uppsala, Sweden) gradient at a centrifugal force of 600×g at 20° C. for 20 minutes. MNC and EC were collected from the interfaces of the 40%/75% and 25%/40%, respectively. Cells isolated from five mice at each day during the time-course following HSV infection were pooled for the following experiments.

(Flow Cytometry)

Cells were stained by a method described in "Inagaki-Ohara, K., Kobayashi, N., Nishimura, H., Sakai, T., Matsumoto, Y., Hiromatsu, K., Awaya, A., and Yoshikai, Y. (1996), Cell immunol. 171, 30-40". Monoclonal antibodies (mAbs) used in the present invention were purchased from PharMingen (SanDiego, Calif.): FITC-conjugated anti-CD3 mAb (145-2 C11), anti-CD11b mAb (M1/70), anti-CD40 mAb (3/23), anti-Iad mAb (AMS-32.1), PE-conjugatedanti-CD4mAb(RM4-5), anti-CD45/B220 (RA3-6B2), anti-CD40L mAb (MR1), biotin-conjugated anti-CD8α mAb (53-6.7). Stained cells were analyzed on an EPICS XL flow cytometry (COULTAR, Miami, Fla.).

(Histological Analysis)

Mice were lethally anesthetized and then fixed in PBS (phosphate buffer saline) which contains 4% formaldehyde. The vaginal wall, uterus and rectum were sagittaly cut into blocks and embedded in paraffin. Thereafter, paraffin sections cut 3 μm in thickness were histologically examined by staining with heamatoxylin-eosin. Also, the paraffin sections were immunohistochemically analyzed using a rabbit anti-HSV-2 antiserum in accordance with a method described in "Kurachi, R., Daikoku, T., Tsurumi, T., Maeno, K., Nishiyama, Y., Kurata, T. (1993), Arch Virol. 133, 259-273". Briefly, the sections were deparaffinized and then treated with PBS containing 0.02% (v/v) calcium chloride and 0.25% (v/v) trypsin (Difco, Detroit, Mich.) at 37° C. for 30 minutes, and then immersed in 0.3 volume % hydrogen peroxide methanol solution for 30 minutes. The sections were reacted with anti-HSV-2 antiserum at 4° C. overnight. Biotinylated anti-rabbit IgG (DAKO Japan, Tokyo, Japan) was added to the sections, and allowed to react at 37° C. for 30 minutes. Thereafter, peroxidase-conjugated streptoavidin (DAKO Japan) was added and then allowed to react at 37° C. for 30 minutes. The peroxidase reaction was conducted in 0.05 M Tris buffer (pH 7.6) containing 0.02% diaminobenzidine (Chemical Dojin Inc., Kumamoto, Japan) and 0.015% hydrogen peroxide. Cell nuclei were counter-stained with 2% methylgreen (Chrome, Stuttgart, Germany).

(Measurement of Cytokine in Vaginal Washes by ELISA)

Vaginal washes were collected daily after infection. Cytokine content in the vagina washes was analyzed using mouse IFN-γ, IL-4 (BioSource International, Inc., Camarillo, Canada) and IL-12 with a measurement kit using ELISA (Amersham LIFE SCIENCE, Buckinghamshire, Britain) in accordance with the manufacturer's instructions.

(Statistical Analysis)

The t-test was used to determine significant differences. A p value of less than 0.05 is considered significant.

(Lesions of Genital Organs and Mortality Induced by Wild Type 186, YY2 (US2-deficient Strain 186) or L1BR1 (US3-deficient Strain 186))

Figure 3:
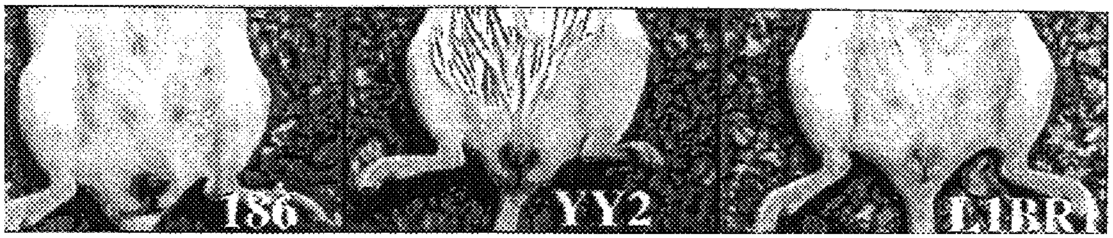
FIG. 3 shows clinical features of BALB/c mice which were intravaginally were infected with $2\times10^4$ PFU of wild type 186, wild type YY2, or L1BR1 after E/DP treatment. Photographs were taken on day 7 after intravaginal infection.
Figure 4:
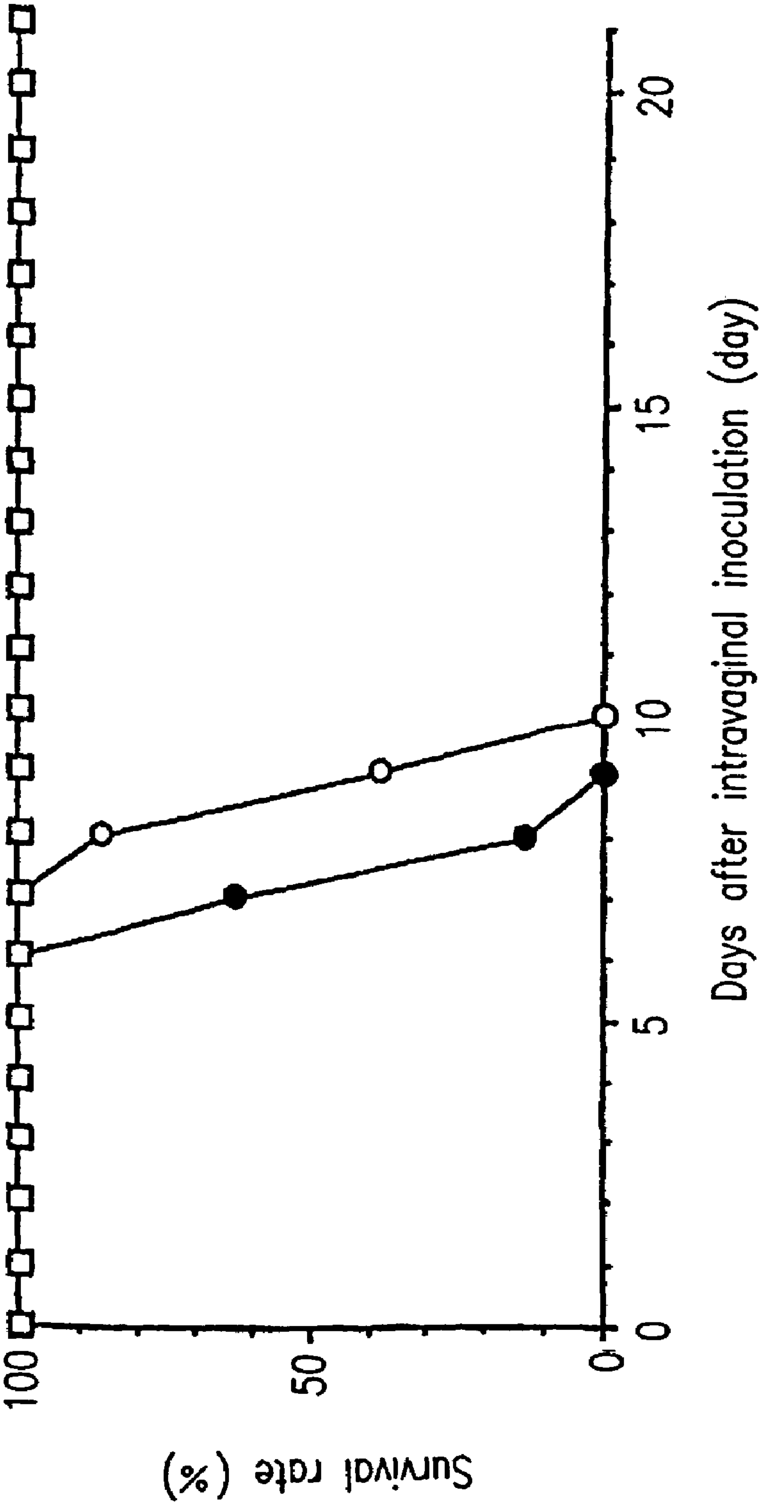
FIG. 4 shows the survival rates of mice which were intravaginally infected with $2\times10^4$ PFU of wild type 186, wild type YY2, or L1BR1. In each case, the number of tests was n=7. It should be noted that in this figure, filled circles indicate wild type 186, unfilled squares indicate wild type YY2, and unfilled circles indicate L1BR1.

To determine the effects of US2 and US3 deletion on pathogenicity, mice were intravaginally infected with $2\times10^4$ PFU of YY2or L1BR1. FIG. 3 shows the representative appearance of the mice after the vaginal infection. The genital organ infected with YY2 started swelling significantly on day 5 after the inoculation (post inoculation; p.i.) as well as the mice infected with wild type 186. For the mice infected with L1BR1, substantially no symptom of vaginal inflammation was observed. The survival rate was shown in FIG. 4. All of the mice infected with wild type 186 or YY2 died within 10 days after the intravaginal inoculation. In contrast, all of the mice infected with L1BR1 survived as long as three weeks after the inoculation.

(Clearance of Virus in the Vagina)

Figure 5:
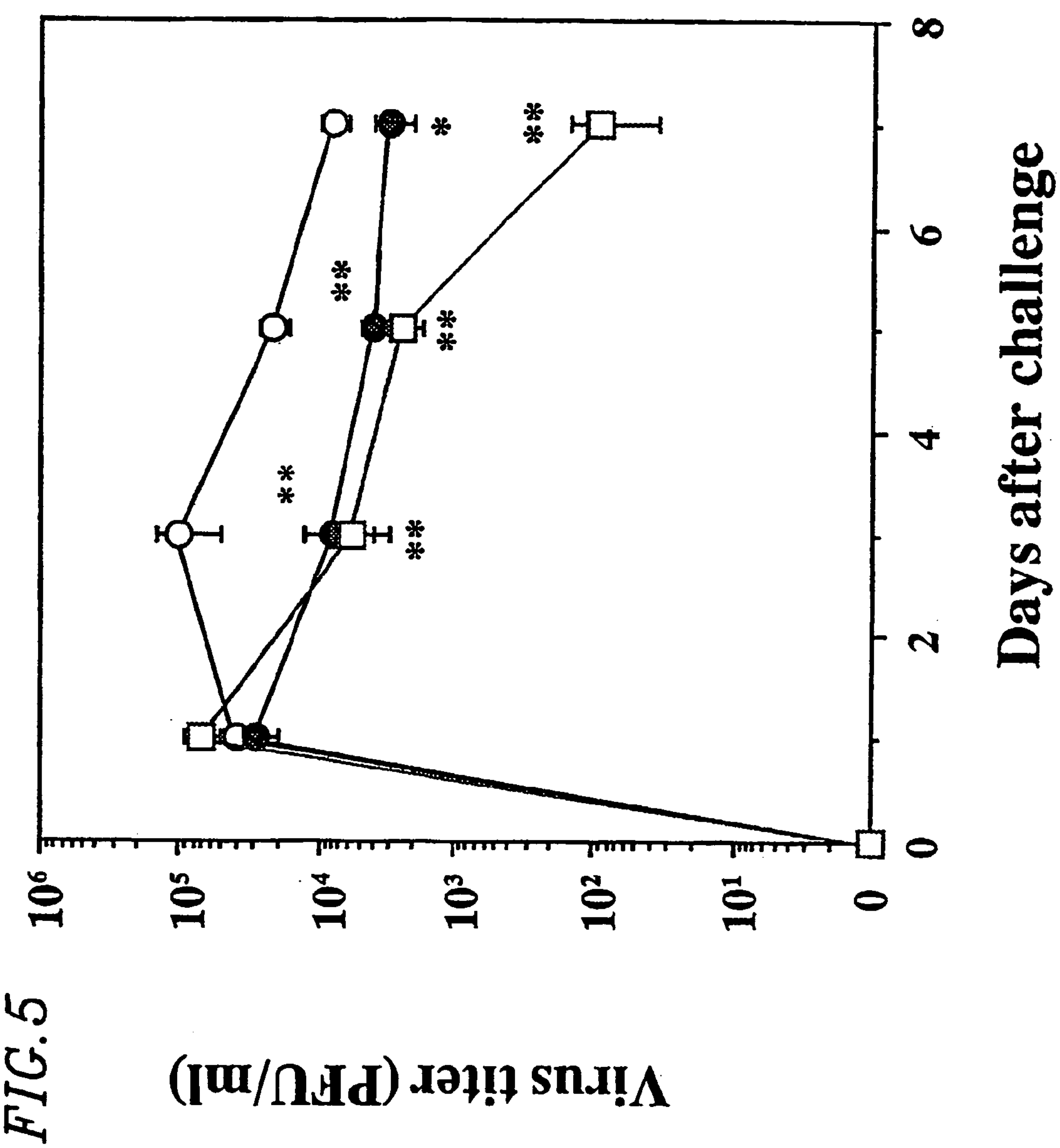
FIG. 5 shows viral clearance from the vaginas of mice infected with wild type 186, wild type YY2 or L1BR1. Vaginal wash on day 0 was collected two hours after intravaginal infection of $2\times10^4$ PFU of wild type 186, wild type YY2 or L1BR1. Values in three separate experiments are represented by ±standard deviation (SD). It should be noted that in this figure, filled circles indicate wild type 186, unfilled squares indicate wild type YY2, and unfilled circles indicate L1BR1. Also, in the figure, ** indicates that a significant difference is $p<0.001$ when compared with values for mice infected with wild type 186. In the figure, * indicates that the significant difference is $p<0.01$.

To compare the rates of viral clearance in vaginal mucosa, mice were intravaginally infected with wild type 186, YY2, or L1BR1 and thereafter viral titers were measured (FIG. 5). The viral titers of the mice rapidly increased and reached the maximum levels at one day post-infection (p.i.). The titers of the mices infected with YY2 and L1BR1 gradually decreased until day 5, while the titers of the mice infected with L1BR1 sharply decreased after day 5. The titers of the mice infected with wild type 186 were sustained until day 3 and thereafter decreased slowly.

(Histopathological Changes of the Vagina)

Figure 6:
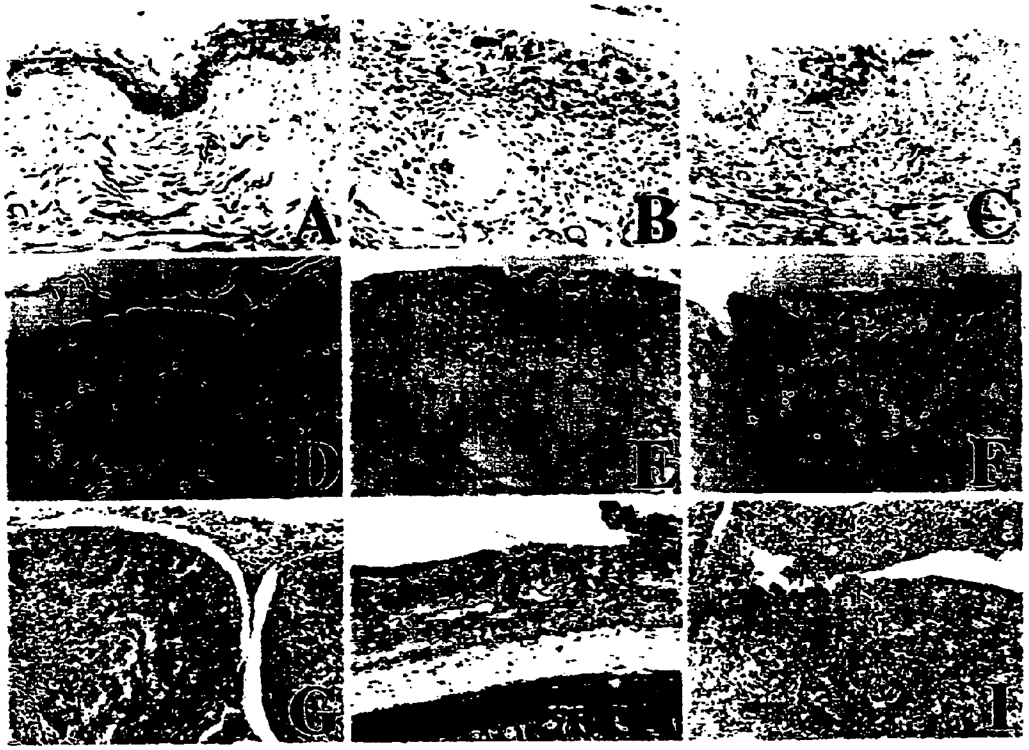
FIGS. 6A through 6F show the vaginal mucosae of BALB/c mice used in histochemical study in examples.

The pathological changes of the vagina and uterus in mice sacrificed at 1, 3, 5 and 7 days post-infection (p.i.) were examined. For all of the mice, viral infection was observed in squamous cells in the epithelial tissue on day 1 (FIGS. 6A, 6B and 6C). By histological analysis, multinucleated giant cells and intranuclear inclusions were observed in squamous cells, and HSV-2 antigens were also detected in these cells (FIGS. 6D, 6E and 6F). Until day 3, no significant changes were observed in the lesions. In this example, viral infection extended to the squamous cells in the epithelial tissue of the vulva and the skin, and reached the nerve plexus in the subepithelium of the mice infected with wild type 186 and YY2. However, such viral spread was not observed in the mice infected with L1BR1. Instead, sub-epithelial infiltration of mononuclear cells was observed on day 5 post inoculation (p.i.) (FIGS. 6G, 6H and 6I).

(Reaction of Cells in the Vagina)

Figure 7:
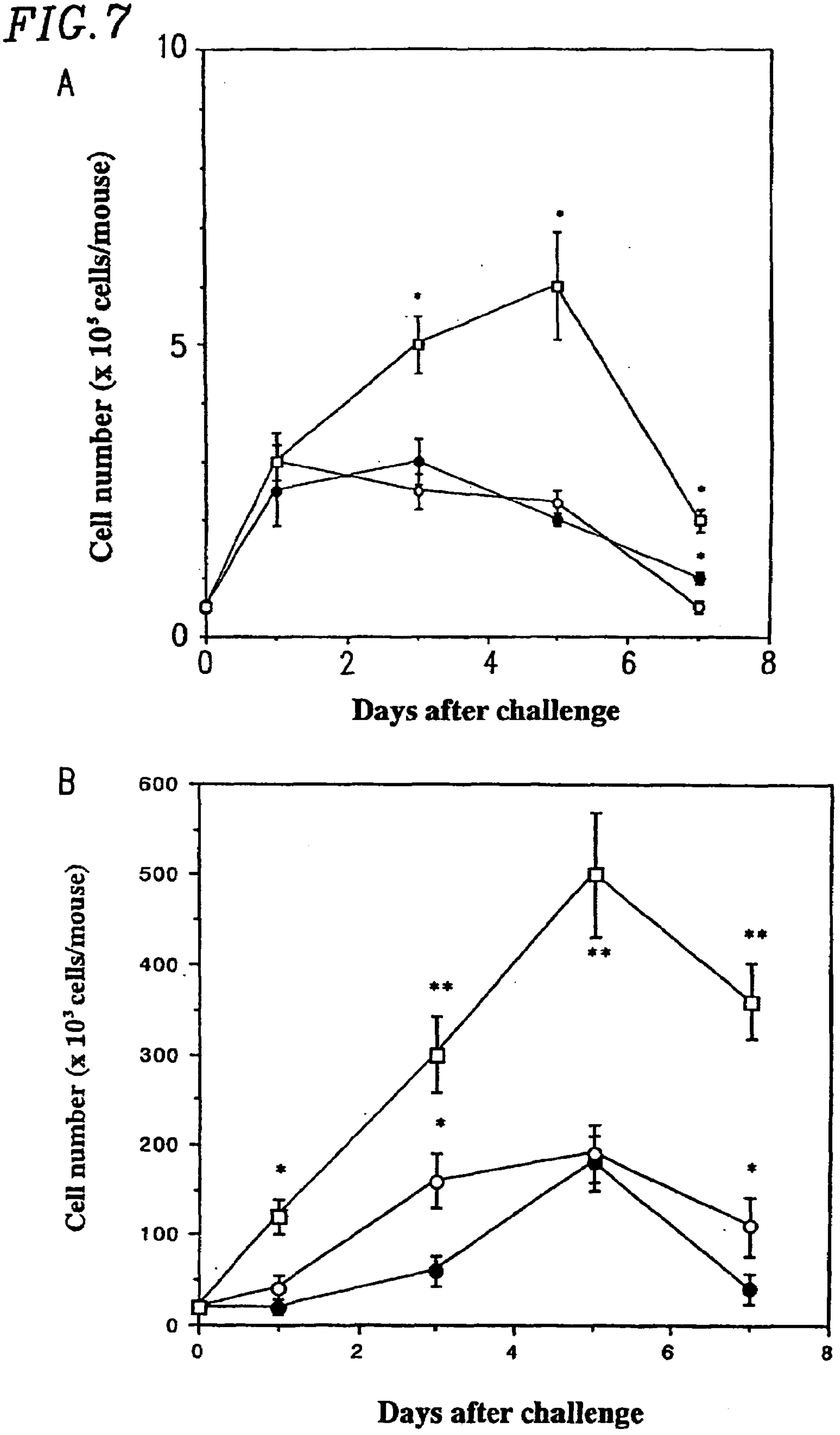
FIG. 7A shows the number of vaginal MNCs infected with wild type 186, wild type YY2 or L1BR1. The number of vaginal MNCs was measured by counting surviving cells stained with trypan blue, which were collected from mice infected with each virus. It should be noted that in this figure, filled circles indicate wild type 186, unfilled squares indicate wild type YY2, and unfilled circles indicate L1BR1.
FIG. 7B shows the kinetics of Fas expressed in vaginal EC. Vaginal EC isolated from mice infected with wild type 186, wild type YY2, or L1BR1 was stained with anti Fas mAb.

Next, the number of mononuclear cells (MNC) isolated from the vagina was measured. As shown in FIG. 7A, the number of MNC in the mice infected with L1BR1 increased until day 5 and thereafter rapidly decreased. However, for the mice infected with wild type 186 or YY2, the numbers of MNC increased on day 1 but thereafter did not increase. On day 3 post inoculation (p.i.), a slow decrease was observed. Such specific reaction kinetics is closely related to histological changes in the vaginal wall. As can be seen from these results, a delay in clearing viruses in the mice infected with wild type 186 or YY2 led to a high case fatality rate.

(Measurement of Expression Level of Fas Antigen)

As shown in FIG. 7B, the number of $Fas^+$ cells was greater in the mice infected with L1BR1 than the mice infected with wild type 186 or YY2 until day 5. Most of the $Fas^+$ cells were positive for MHC class II antigen I-$A^d$ (data not shown). According to this, it was found that the number of $Fas^+$ vaginal ECs was significantly greater in the mice infected with L1BR1 than in the mice infected with wild type 186 or YY2 at the early phase of the infection.

(Measurement of Reaction Kinetics of Appearance of APC and T Cells in Vagina)

Figure 8:
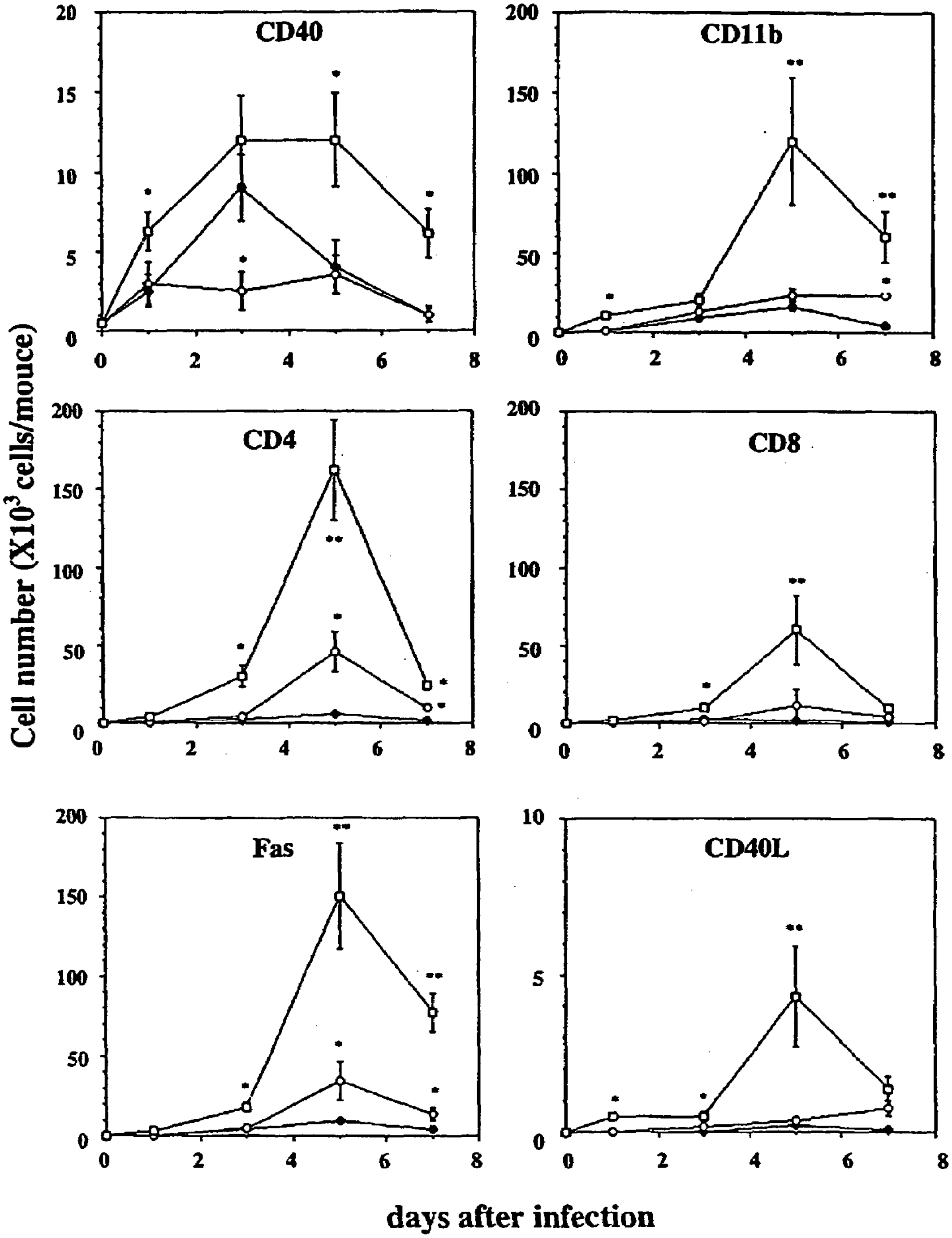
FIG. 8 shows vaginal MNCs isolated from HIV-infected mice, which were stained with CD11b and CD40 for detection of APC, and with labeled mAb for detection of T cell. Values in three separate experiments are represented by ±standard deviation (SD). In the figure, ** indicates that a significant difference was $p<0.001$ when compared with values for mice infected with wild type 186. In the figure, * indicates that the significant difference was $p<0.01$.

As can also be seen from FIG. 8, CD40 and CD11b were used as representative markers for DC and Mϕ, respectively. The number of $CD40^+$ cells rapidly increased in the mice infected with L1BR1, and was consistently greater. than in the mice infected with wild type 186 or YY2 throughout the experiment. On day 3, the number of $CD11b^+$ cells only slightly increased. However, on day 5, a significant increase was observed in the mice infected with L1BR1. Concerning T cells, the numbers of $CD4^+$, $CD8^+$, $CD40L^+$ and $Fas^+$ T cells reached the respective maximum levels on day 5 and thereafter decreased. CD40L as well as Fas was expressed in activated T cells. The numbers of $Fas^+$ and $CD40L^+$ cells was much greater in the mice infected with L1BR1 than in the mice infected with wild type 186 or YY2. The numbers reached the respective maximum levels on day 5. These results indicate that induction/activation of vaginal APC and T cells in the mice infected with L1BR1 is more rapid and greater in magnitude than in the mice infected with wild type 186 or YY2.

(Cytokines Secretion in Vaginal Washes)

Figure 9:
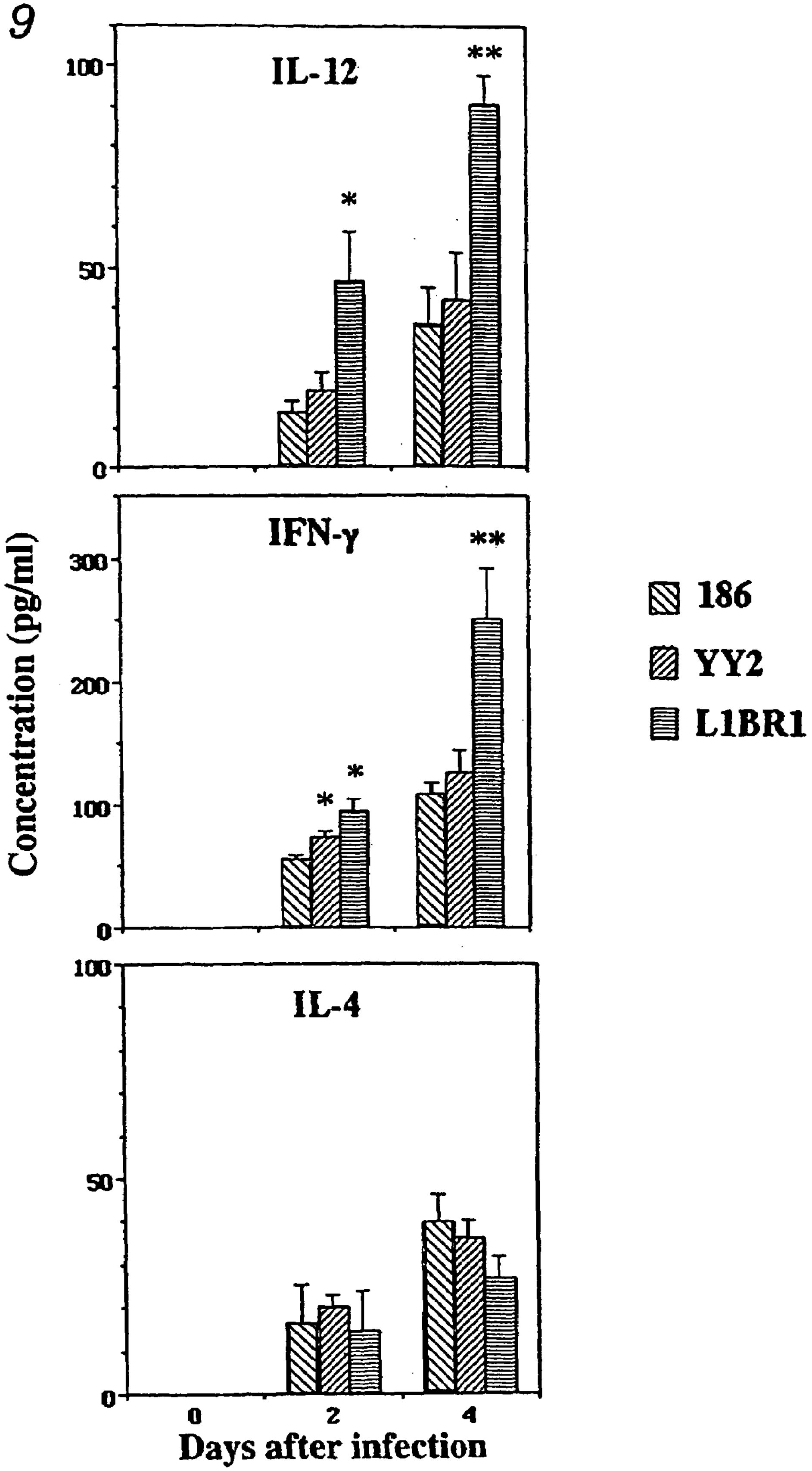
FIG. 9 shows the amount of cytokines generated in vaginal wash. The vaginal wash was collected from mice infected with wild type 186, wild type YY2, or L1BR1 on day 0, 2, and 4. The levels of IL-12, IFN-γ and IL-4 were measured by ELISA. Values in three separate experiments are represented by ±standard deviation (SD). In this figure, ** indicates that a significant difference is $p<0.05$ when compared with values for mice infected with wild type 186. In the figure, * indicates that the significant difference is $p<0.01$.

Production of cytokines is required for protecting hosts from viral pathogens. The production level of cytokines was examined on day 2 by ELISA. As a result, an increase in production of IL-12 was detected. On day 2 and 4, the IL-12 production was significantly greater in the mice infected with L1BR1 than in the mice infected with wild type 186 or YY2 (FIG. 9). IFN-γ and IL-4 are representative cytokines of Th1 and Th2, respectively. The production pattern of IFN-γ was significantly higher in the mice infected with L1BR1 than in the mice infected with wild type strain 186 on day 4. The production level of IL-4 tended to be lower in the mice infected with L1BR1 than in the mice infected with wild type strain 186. The production patterns and levels of both cytokines in the mice infected with YY2 were similar to those in the mice infected with wild type 186. These results indicate that cytokine production biased towards Th1 was induced in the mice infected with L1BR1.

The US3-deficient HSV gene recombinant contained in the vaccines of the present invention was considerably attenuated. Therefore, when the US3-deficient HSV gene recombinant is inoculated into an organism, the organism exhibits no or substantially no symptom of the infection. Nevertheless, the US3-deficient HSV gene recombinant can activate the immune function of infected patients against HSV infection. Therefore, the severity and/or infection rate of HSV infection can be reduced, so that diseases caused by HSV infection can be prevented and/or treated. Since the US3 gene is not necessarily essential for virus replication, the US3-deficient HSV gene recombinant can be multiplied within the body of an organism to which the gene recombinant has been inoculated, so that immune activity against HSV infection can be sustained for a long time.

Example 9

Comparison of HF (MNO10) with Antitumor Function of UL39-inactivated HSV

Tumor cell strain NfSaY83 derived from C3H mouse was transplanted into groups of CH3 mice (6 weeks old, each group includes 10 mice) by intraperitoneally injecting $1\times10^7$ cells/mouse under ether anesthesia. After the transplantation, $1\times10^7$ PFU/mouse of UL39-inactivated virus or HF strain clone 10 (UL56-deficient virus) was intraperitoneally injected into the respective groups on day 7. Second injection was conducted for the group, to which the UL39-inactivated virus had been administered, on day 12 after the transplantation. The survival time was compared. Only cancer cells were inoculated to mice as a control. The results are shown in FIG. 11.

Figure 11:
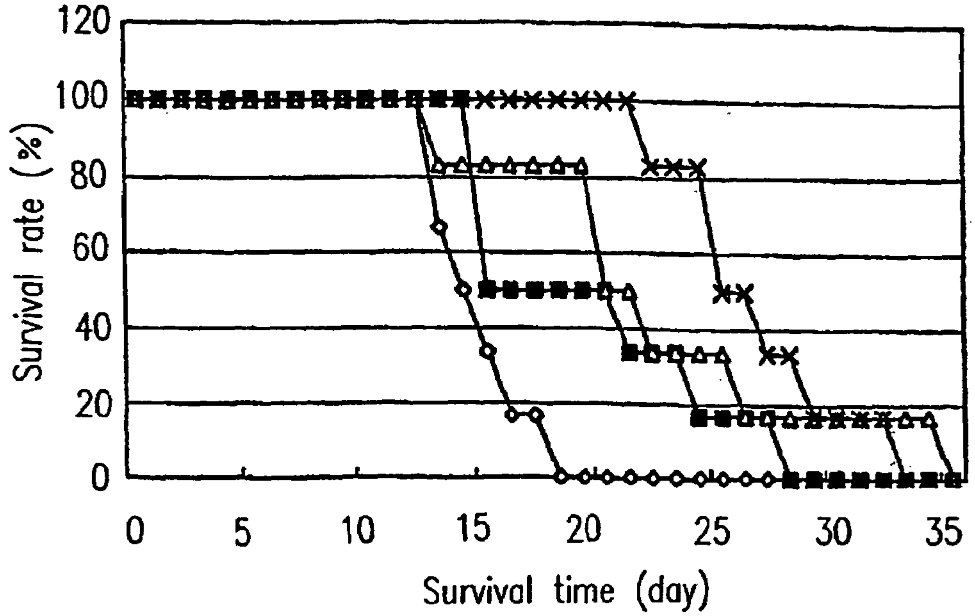
FIG. 11 is a diagram showing comparison of survival time between UL56-deficient HSV (strain HF; MNO10) inoculation and UL39-inactivated HSV inoculation. In the figure, unfilled diamonds indicate a control, filled squares indicate mice given the UL39-inactivated HSV at one time, unfilled triangles indicate mice given the UL39-inactivated HSV at two times, and crisscrosses indicate mice given strain RF at one time.

The results of FIG. 11 clearly indicate that all of the groups exhibited a survival rate of 100% until day 13, thereafter the survival time was more elongated when HF strain clone 10 was inoculated once than when the UL39-inactivated virus was inoculated twice.

Example 10

Effect of Consecutive Administration of HF (MNO10)

Tumor cell strain NfSaY83 derived from C3H mouse was transplanted into groups of CH3 mice (6 weeks old, each group includes 10 mice) by intraperitoneally injecting $5\times10^6$ cells/mouse under ether anesthesia. After the transplantation, $1\times10^7$ PFU/mouse of HF (UL56-deficient virus) was intraperitoneally injected into one group on three consecutive days, i.e., day 7, 8 and 9. The survival time was compared. Only cancer cells were inoculated to mice as a control. The results are shown in FIG. 12.

Figure 12:
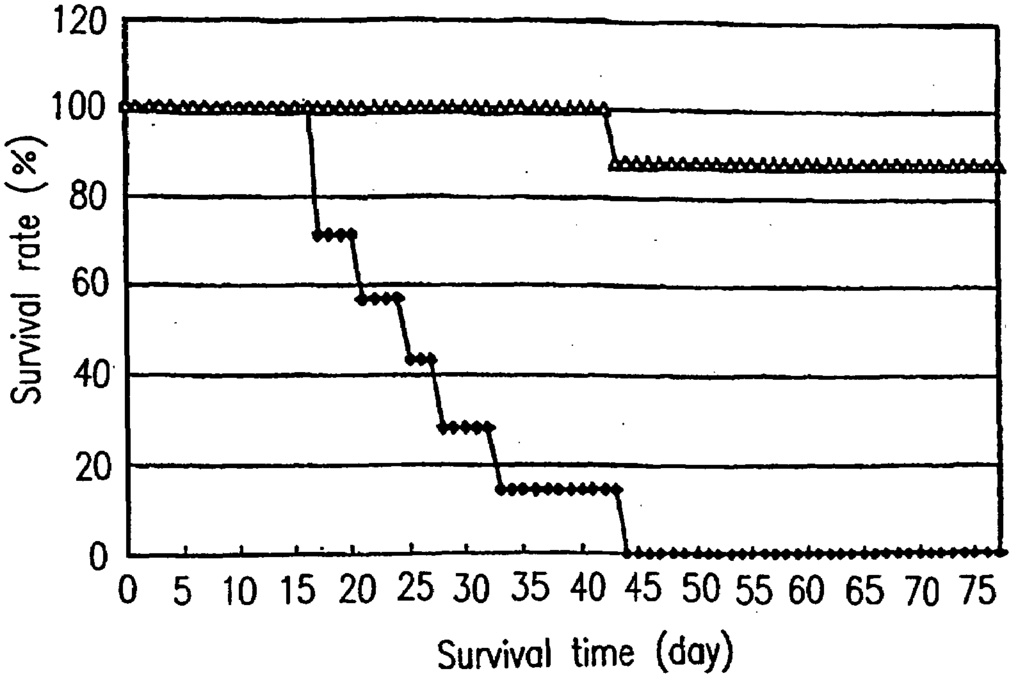
FIG. 12 is a diagram showing the survival time when UL56-deficient HSV (MNO10) were consecutively administered. In the figure, filled diamonds indicate a control, and unfilled triangles indicate mice consecutively given strain HF. The body weight change thereof is also shown.
Figure 12:
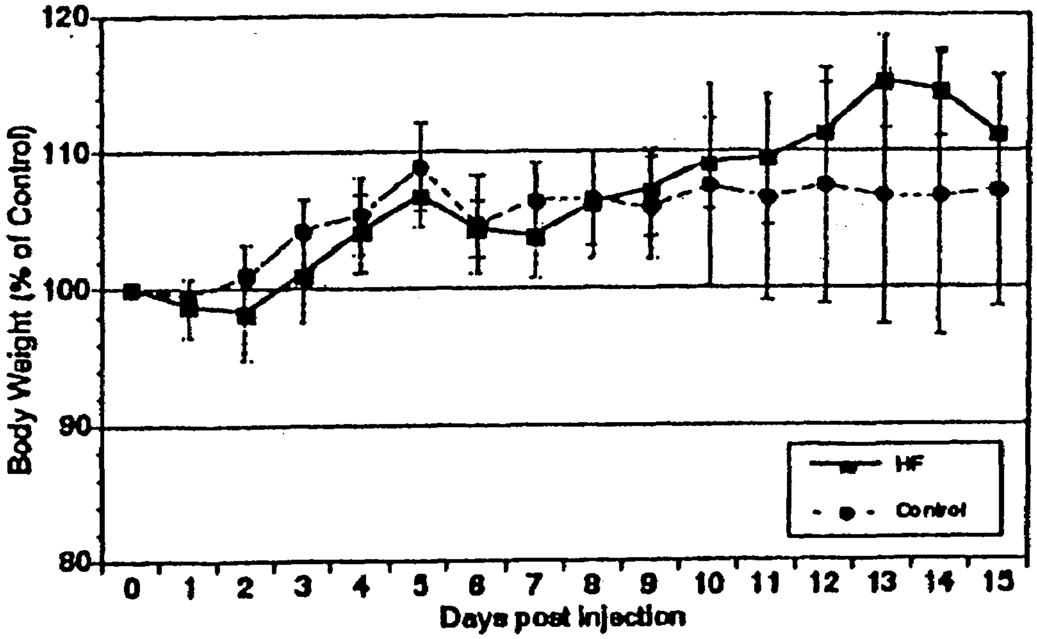

The results of FIG. 12 indicate that all of the groups exhibited a survival rate of 100% until day 17 and thereafter, the survival time was more elongated by consecutively administering the virus.

Example 11

$1\times10^7$ PFU of the attenuated HSV of the present invention (MNO10), 1.8 g of glucose, and 0.06 g of sodium citrate were dissolved in 80 ml of water for injection. The solution was adjusted to pH 6.3 by adding sodium hydrate, and to a total volume of 100 ml by adding water for injection. Thereafter, the resultant solution was subjected to filtration, and then 500 ml thereof was loaded into a gas-permeable plastic container (made of PP). This container was subjected to steam sterilization under high pressure at 116° C. for 14 minutes. Thereafter, the container was wrapped with a secondary wrapping material (alumina deposition film), followed by vacuum packaging or nitrogen gas filling, thereby obtaining an injection.

When the attenuated HSV of the present invention in which UL56 is inactivated is used, a single administration can prolong the life time more than when the UL39-inactivated virus, i.e., attenuated HSV strain is consecutively administered.

Further, if the attenuated HSV of the present invention is consecutively administered, a higher level of life prolongation effect can be obtained. Therefore, it was demonstrated that the attenuated HSV of the present invention is useful for pharmaceutical compositions for treating malignant tumor.

Example 12

Antitumor Action of US3-deficient HSV-2 Virus and US3- and UL56-inactivated HSV (HL)

Next, the US3-deficient HSV-2 virus and the US and UL56-inactivated HSV (HL) were examined for their antitumor functions.

(Viruses Used)

Figure 13A:
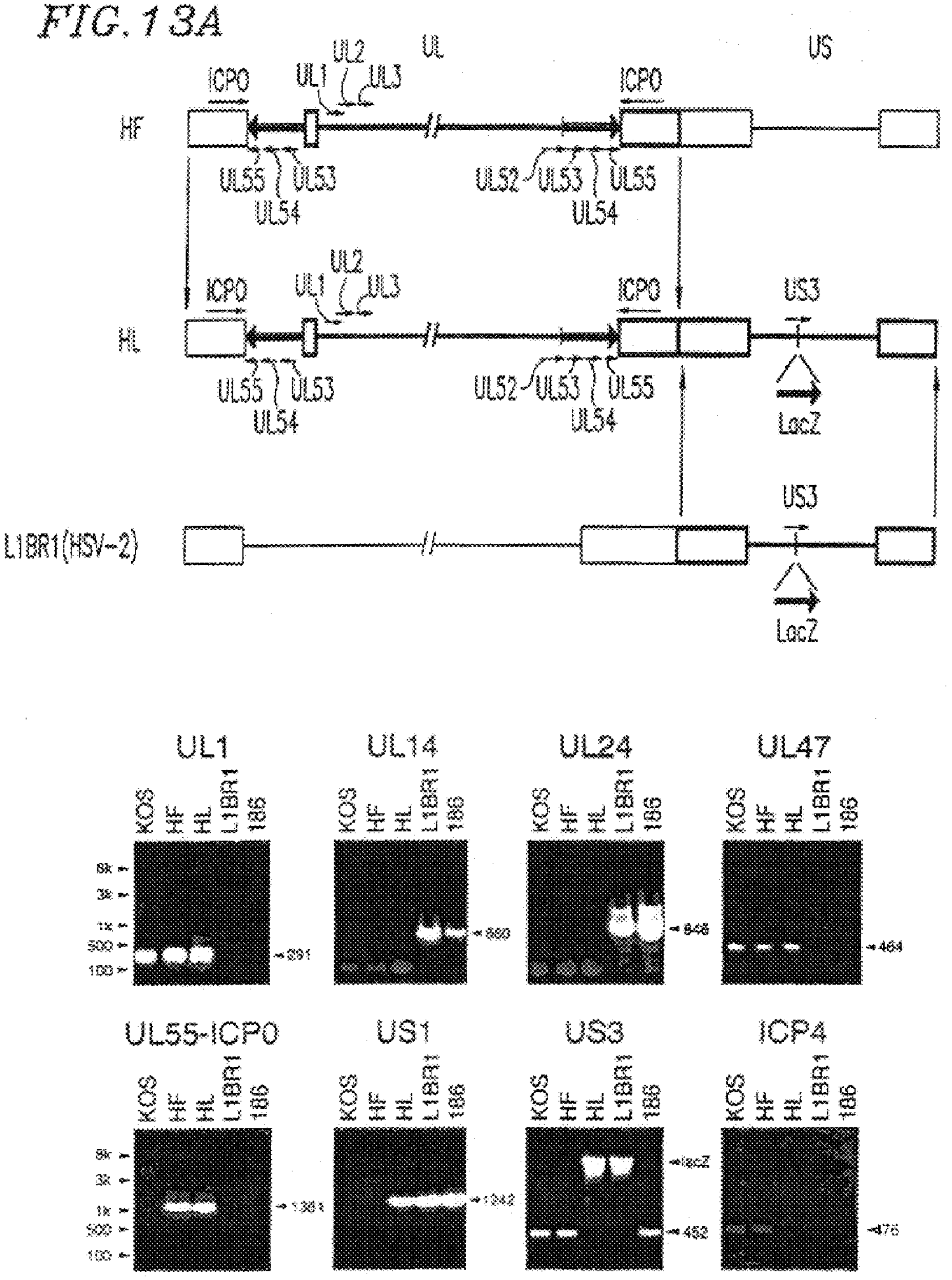
FIG. 13A is a diagram showing the structure of a genome used in Example 9. L1BR1 is HSV-2 in which the US3 gene thereof is inactivated. HF is HSV-1 in which the UL56 gene thereof is inactivated. HL is a hybrid of L1BR1 and HF. A L region is HSV-1 while-a S region is HSV-2. Both UL56 and US3 are deficient. The genome structure is confirmed by the PCR analysis below.
Figure 13C:
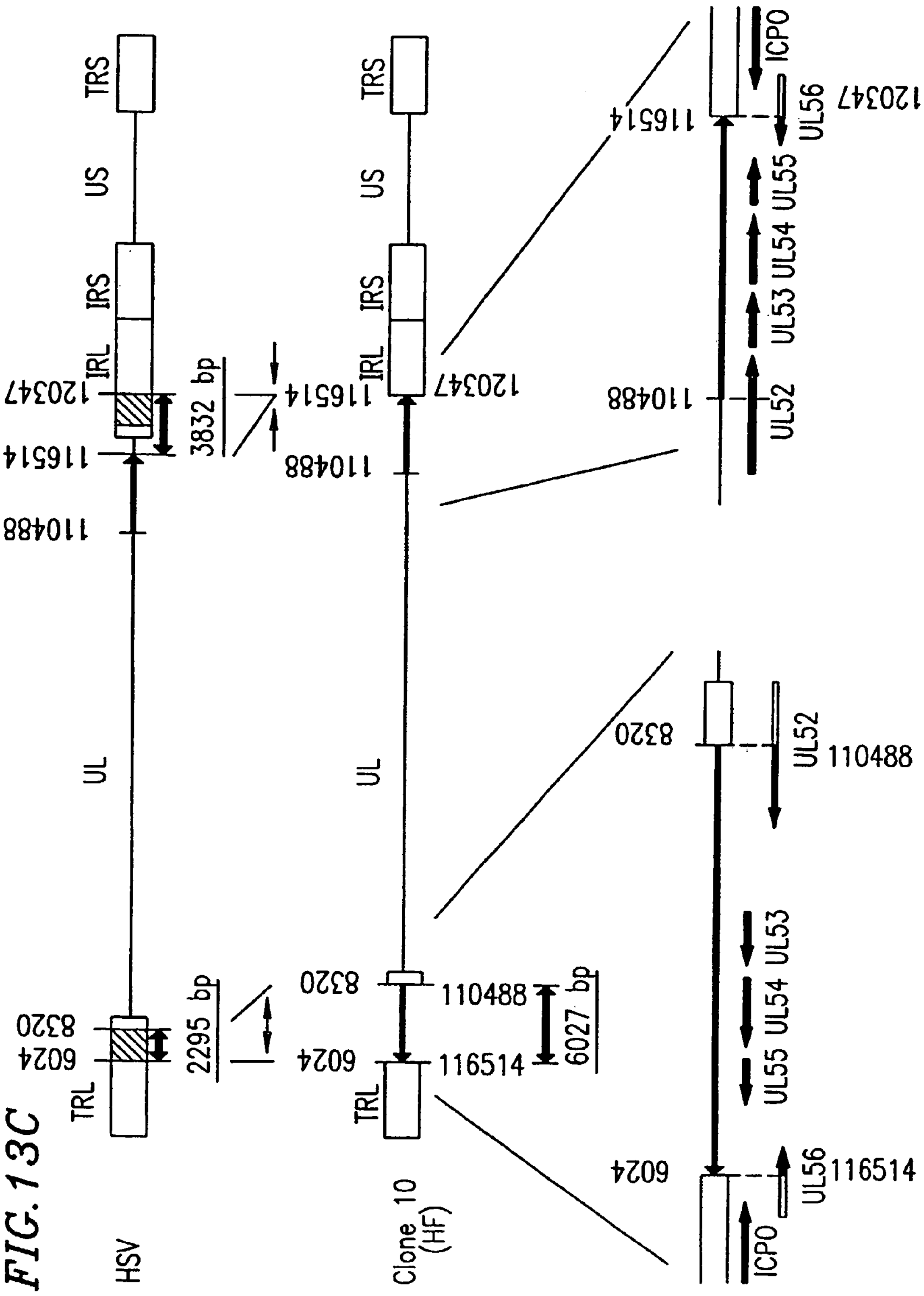
FIG. 13C is a diagram for explaining inactivation of HF in detail.

The following viruses were used in Example 9. The structure of the viruses is shown in FIG. 13.

1) HSV-2 US3Δ (L1BR1)

Mutated virus derived from wild type HSV-2 (strain 186), in which the US3. gene was inactivated by inserting a lacZ cassette. This virus was prepared as described in Example 4.

2) HSV HL

Recombinant virus from HSV-1 HF and HSV-2 US3Δ. The L region thereof is mainly derived from HSV-1 HF, and the S region thereof is derived from HSV-2. This recombinant virus is prepared by mixed infection with the above-described two viruses, forming cell fusion, and separating viruses forming a blue plaque in the presence of X-gal. Thereafter, the structure of the gene was confirmed by PCR. HL virus lacks the US3 and UL56 genes.

3) HSV-1 UL39-inactivated HSV

The viruses used in the above-described examples were used as controls.

(Mice)

Figure 14:
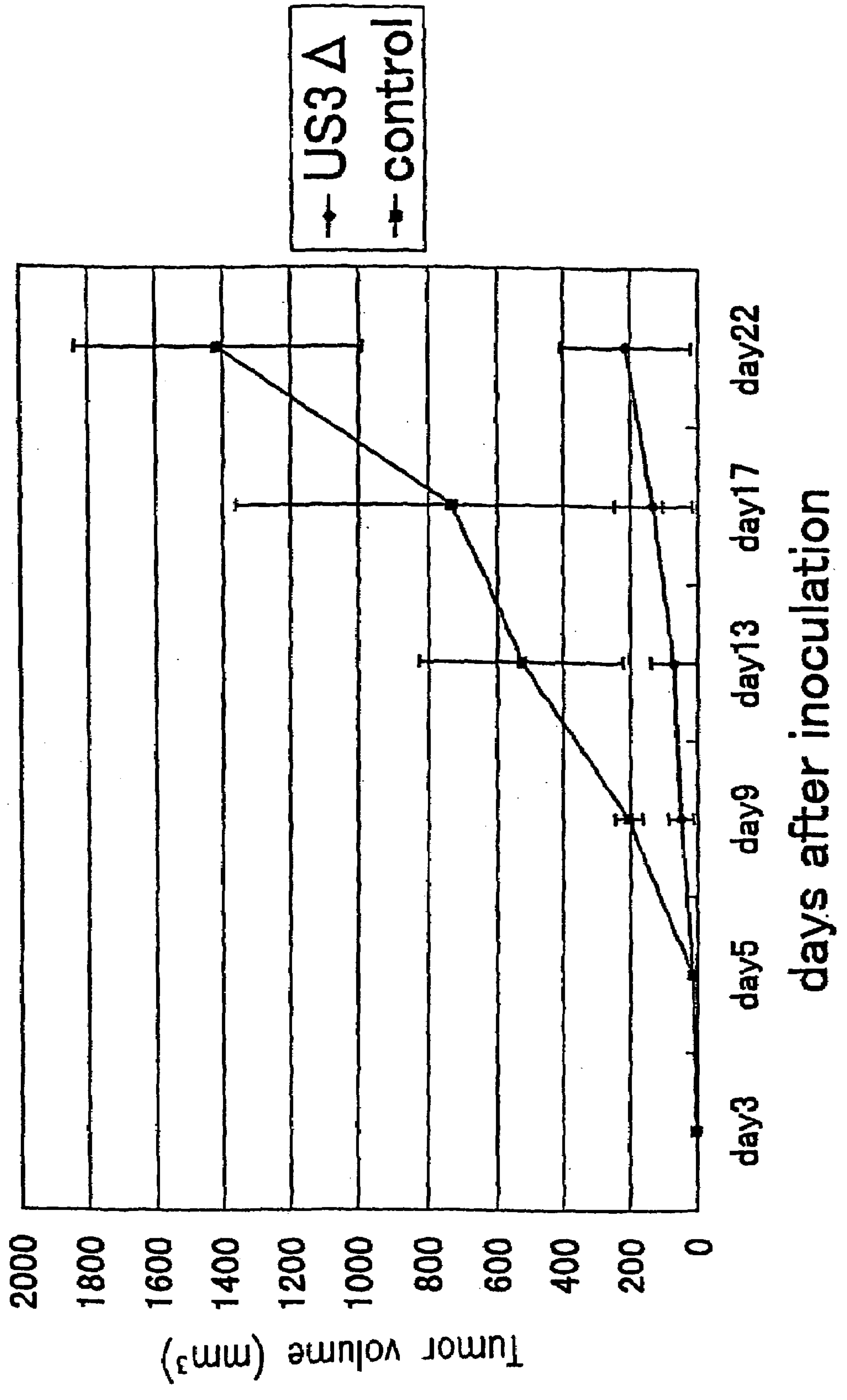
FIG. 14 is a graph showing the antitumor effect of HSV-2 in which the US3 gene thereof is inactivated.
Figure 15:
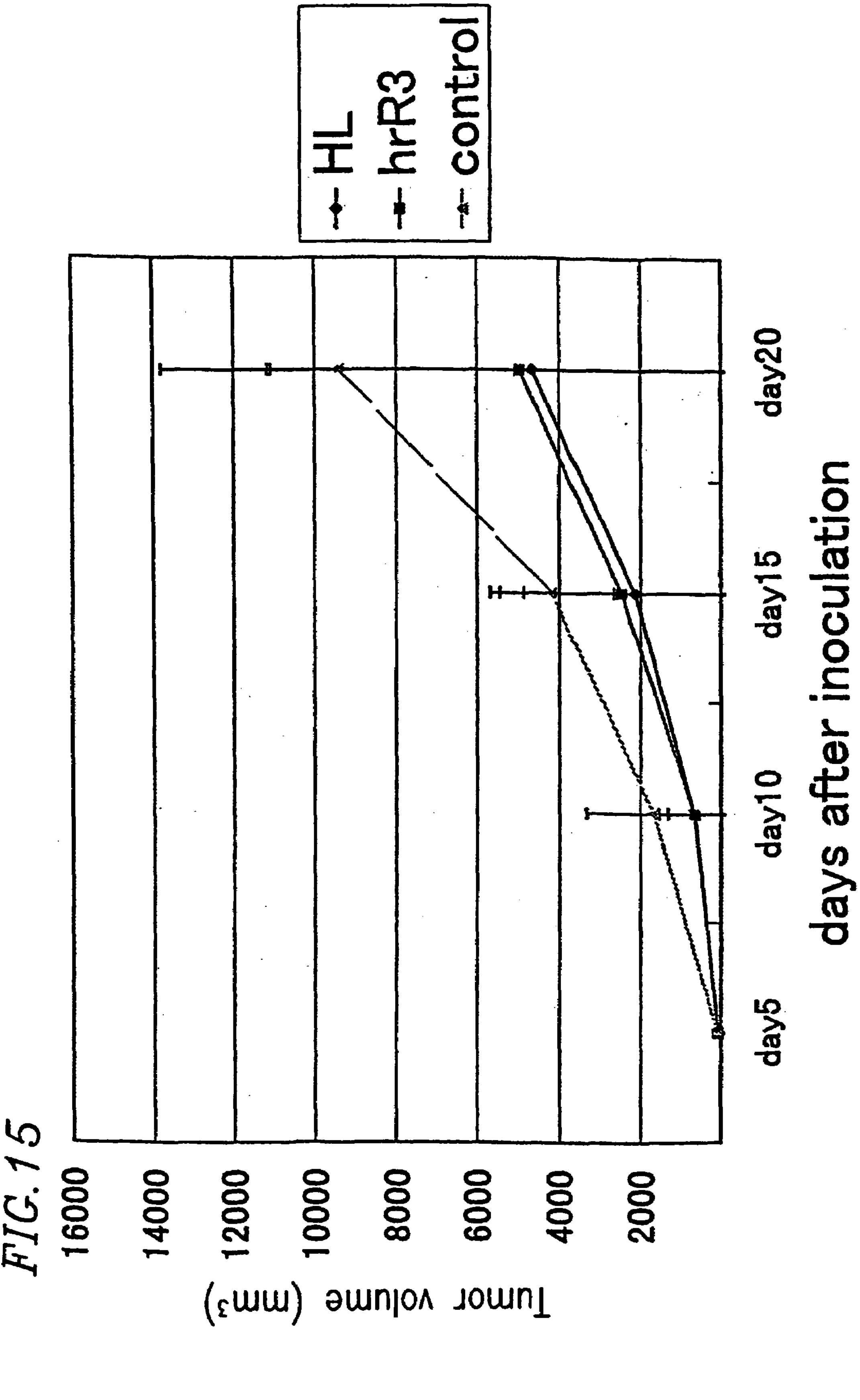
FIG. 15 is a graph showing the antitumor effect of HSV-2 in which the UL56 gene thereof is inactivated.

Tumor cell strain NfSaK derived from C3H mouse was transplanted into groups of CH3 mice (6 weeks old, each group includes 10 mice) by intraperitoneally injecting $1\times10^7$ cells/mouse at their backs and necks under ether anesthesia. On day 7 after the transplantation, $1\times10^7$ PFU/mouse of HSV-2 US3Δ, or PBS (control), was injected into the mice in which tumor cells were injected to the backs thereof, while $1\times10^7$ PFU/mouse of HL and HrR3, or PBS (control), were injected into the mice in which tumor cells were injected to the necks thereof. The survival time was compared. The results are shown in the following Table and FIGS. 14 and 15.

TABLE

Action of HSV-2 US3Δ on melanoma solid tumor (back)
(Number of surviving mice (rate))

| Control (PBS inoculation) | |
|---|---|
| Day 1–16 | 5/5 (100%) |
| Day 17 | 4/5 |
| Day 24 | 2/5 |
| Day 25 | 1/5 |
| Day 37 | 0/5 (0%) |

TABLE-continued

Action of HSV-2 US3Δ on melanoma solid tumor (back)
(Number of surviving mice (rate))

| HSV-2 US3Δ inoculated group | |
|---|---|
| Day 1–26 | 5/5 (100%) |
| Day 27 | 4/5 |
| Day 32 | 3/5 |
| Day 42 | 2/5 |
| Day 60 | 2/5 (40%) |

Action of HSV on NfSak solid tumor (neck)
(Number of surviving mice (rate))

| Control (PBS inoculation) | |
|---|---|
| Day 1–22 | 5/5 (100%) |
| Day 23 | 4/5 |
| Day 25 | 3/5 |
| Day 30 | 2/5 |
| Day 31 | 0/5 (0%) |
| HL inoculated group | |
| Day 1–27 | 7/7 (100%) |
| Day 28 | 6/7 |
| Day 30 | 5/7 |
| Day 32 | 4/7 |
| Day 60 | 4/7 (57%) |
| HSV-1 UL39-inactivated HSV inoculated group | |
| Day 1–23 | 7/7 (100%) |
| Day 24 | 6/7 |
| Day 25 | 5/7 |
| Day 34 | 4/7 |
| Day 35 | 3/7 |
| Day 36 | 2/7 |
| Day 60 | 2/7 (28%) |

It was demonstrated that when the attenuated HSV of the present invention in which US3 is inactivated is used, a single administration can prolong the life time.

Example 13

Antitumor Effect of Hh

Next, the antitumor effect of the UL39- and UL56-inactivated HSV (Hh) was demonstrated.

BALB/c mice (6 weeks old, each group includes 6 to 7 mice) were used as subject animals. Cancer Colon26 (Dr. Shuji Hayashi, Department of Surgery, Nagoya University School of Medicine; a cell strain derived from large intestine cancer of BALB/c mice) was intraperitoneally inoculated at $5\times10^6$ cells/mouse. HSV-1 Hh prepared in Example 2 was used as the virus control in PBS inoculation.

(Mode 1)

After the inoculation of the tumor cells, $1\times10^7$ PFU of Hh virus was intraperitoneally inoculated on day 7 and its survival curve was compared with the controls (PBS inoculation). The results are shown below.

TABLE

| Antitumor effect of Hh | | | | | |
|---|---|---|---|---|---|
| | Days after antitumor inoculation | | | | |
| | Day 15 | Day 30 | Day 45 | Day 60 | Day 75 |
| Hh inoculation group | 6/6 | 5/6 | 4/6 | 4/6 | 4/6 |
| Control group | 6/6 | 5/6 | 4/6 | 2/6 | 2/6 |

(Mode 2)

After the inoculation of tumor cells, $1\times10^7$ PFU of Hh virus was inoculated consecutively on day 8, 9 and 10 and its survival curve was compared with the controls. The results are shown below.

TABLE 2

| Effect of consecutive three administrations | | | |
|---|---|---|---|
| | Days after antitumor inoculation | | |
| | Day 30 | Day 45 | Day 60 |
| Hh inoculation group | 7/7 | 7/7 | 7/7 |
| Control group | 5/7 | 4/7 | 2/7 |

As described above, Hh exhibited a significant antitumor effect as compared to the control group. Particularly, Hh having a significantly improved safety led to 100% survival when administered three consecutive times. Moreover, when these surviving mice were challenged again with Colon26 at $1\times10^7$ cells/mouse, 100% of the mice survived. This demonstrated establishment of antitumor immunity.

Example 14

L1BR1

In this example, the effect of the gene recombinant HSV-2186, which does not express US3, as prepared in Example 9 on solid tumor was demonstrated.

Female mice C3H/He (6 weeks; each group includes 5 mice) were used as subject animals. As tumor cells, NfSaY83 used in the above-described examples was used.

The hair of the back was shaved and $1.25\times10^6$ cells/0.1 ml of NfSa was inoculated on the back.

After the inoculation of the tumor cells, 0.1 ml of L1BR1 ($1\times10^7$ cell PFU/0.1 ml) was inoculated to a tumor portion three times.

Evaluation was carried out based on the number of surviving mice and change in the size of tumor (volume). The results are shown in the following table.

TABLE

| Transition in volume ($mm^3$) of tumor after inoculation of tumor (individual results) | | | | | |
|---|---|---|---|---|---|
| | Day 10 | Day 20 | Day 30 | Day 40 | Day 50 |
| L1BR1 inoculation group | 5 | <5 | <5 | <5 | <5 |
| | 9 | 54 | 150 | 545 | Dead |
| | <5 | <5 | <5 | <5 | <5 |
| | 24 | <5 | <5 | <5 | <5 |
| | 13 | <5 | <5 | <5 | <5 |
| Number of surviving mice | 5/5 | 5/5 | 5/5 | 5/5 | 4/5 |
| Control group | 21 | 186 | 1210 | Dead | |
| | 42 | 419 | Dead | | |
| | 73 | 420 | Dead | | |
| | 42 | 161 | 1346 | 4300 | Dead |
| | 142 | 266 | 486 | Dead | |
| Number of surviving mice | 5/5 | 5/5 | 3/5 | 1/5 | 0/5 |

As described above, L1BR1 (US-deficient HSV-2) exhibited an excellent antitumor effect on solid tumor.

Example 15

Use of Attenuated HSV for HIV Therapy

Next, it is demonstrated that another disease can be treated or prevented using the attenuated HSV of the present invention.

A nucleic acid sequence having a promoter for the immediate early gene of human cytomegalovirus at its upstream portion and a sequence encoding an envelope protein, HIV gp120, is inserted to a lacZ gene (open reading frame) so that DNA in which the lacZ gene is interrupted by the necleic acid sequence is prepared.

Vero cells are transfected with this DNA and infectious DNA derived from the UL56- and UL39-inactivated virus (the attenuated HSV (HR522) prepared in Example 5). Produced viruses are collected.

Viruses which produced colorless plaque in the presence of X-gal are collected, followed by plaque cloning. The resultant viruses are stored as a primary stock. Cell samples are infected with clones obtained as the primary stock. The infected cell samples are subjected to a fluorescent antibody technique using tag antibodies. For positive clones, a secondary stock is prepared. The finally obtained clones are subjected to dot blotting using commercially available anti-gp120 antibodies to test the presence of gp120. A gp120-positive strain is used in the following experiment.

Thereafter, the attenuated HSV which expressed HIV gp120 can be used to prevent a human from being infected with HIV or treat a human infected with HIV. The effect of the attenuated HSV of the present invention may be advantageous over conventional drug therapies.

As the above-described HIV antigen, gp41 and gp17 matrix proteins, p24 capsid protein, reverse transcriptase (HIV pol), tat rev, and the like may be used as well as gp120.

Therefore, it is demonstrated that the attenuated HSV of the present invention is effective to an infectious disease caused by an infectous pathogen other than herpes virus-related pathogens.

INDUSTRIAL APPLICABILITY

The present invention provides a method for effectively treating various diseases (e.g., infectious diseases or cancer). The present invention provides a sustaining effect, with few side effects, against herpes virus-related diseases, tumor, and the like, for which there is conventionally no effective treatment method. These are considered as advantageous effects. Production of compositions, virus constructs, kits, medicaments, and the like for use in the treatment method of the present invention is sufficiently industrially applicable. The present invention (compositions and the like) can be practiced by doctors and further, for example, pharmaceutical companies in their business. Therefore, the present invention is considered to be sufficiently industrially applicable. The method of the present invention is useful for a therapeutic method for purely therapy purposes and further clinical trial for business purposes. Therefore, the method of the present invention is industrially applicable. The therapeutic method of the present invention may be practiced indirectly or directly in the marginal industries of medical business, and therefore is sufficiently industrially applicable.

The invention claimed is:

1. A herpes virus, wherein at least two non-essential genes for replication thereof are inactivated and further wherein the herpes virus is herpes simplex virus, wherein the first non-essential gene is UL56 and the second non-essential gene for replication is UL43.

2. The herpes virus according to claim 1, wherein the second non-essential gene for replication is a gene not involved in DNA and deoxyribonucleotide metabolism.

3. The herpes virus according to claim 2, wherein the gene not involved in DNA and deoxyribonucleotide metabolism is UL43.

4. The herpes virus according to claim 1, wherein the second non-essential gene for replication is UL43.

5. The herpes virus according to claim 1, further comprising an exogenous suicide gene.

6. The herpes virus according to claim 1, further comprising a carboxyesterase gene.

7. The herpes virus according to claim 1, wherein the virus has ability to select cancer cells.

8. The herpes virus according to claim 1, wherein the inactivation includes at least one nucleotide substitution, addition, deletion, or modification in the sequence of the non-essential gene for replication.

9. The herpes virus according to claim 1, wherein the virus is a modified HSV-1 or HSV-2.

* * * * *

```
                              SEQUENCE LISTING


<160> NUMBER OF SEQ ID NOS: 6

<210> SEQ ID NO 1
<211> LENGTH: 900
<212> TYPE: DNA
<213> ORGANISM: Herpes simplex
<220> FEATURE:
<221> NAME/KEY: CDS
<222> LOCATION: (3)..(41)
<223> OTHER INFORMATION:

<400> SEQUENCE: 1

gg gag cag ggg gcg tcg acc cgg gac gag gga aaa caa taa gggacgcccc      51
   Glu Gln Gly Ala Ser Thr Arg Asp Glu Gly Lys Gln
   1               5                   10

ccgtgtttgt ggggaggggg gggtcgggcg ctgggtggtc tctggccgcg cccactacac     111

cagccaatcc gtgtcgggga ggggaaaagt gaaagacacg ggcaccacac accagcgggt     171

ctttagtgtt ggccctaata aaaaaaaact caggggattt ttgctgtcta ttgggaaata     231

aaggtttact tttgtatctt ttccctgtct gtgttggatg gatctcgggg gtgcgtggga     291

gtgggggtgc gtgggagtgg gggtgcgtgg gagtgagggt gcgtgggagt gagggtgcgt     351

gggagtgggg gtgcgtggga gtgggggtgc gtgggagtgg gggtgcgtgg gagtgggggt     411

gcgtgggagt gggggtgaca tgttgggcag gctctggtgt taaccacaga gtcgcggccc     471

gggctgcctg accaccgatc cccgaaagca tcctgccact ggcatggagc cagaaccaca     531

gtgggttggg tgtgggtgtt aagtttccgc gagcgcctgc ccgccgaggc tatgtcggac     591

caccccccaa cctatgccac tgtcgtggcc gttcgttcga ccgaacagcc gtccggggct     651

ttggcgcccg acgaccagcg acgaacgcaa aactcgggcg cgtggcggcc tcctagggtc     711

aattcgcgcg agctgtacag ggcccaacgc gcagcgcgcg gctcgtctga tcatgcccca     771

taccggcgac agggctgttg tggtgtggtg gggcgccatg ctgtatttgg ggtggtcgcg     831

atagtggtgg tcattattct ggtattcctg tggcggtaag cgcccctgtg agttaataaa     891

taaaagtat                                                             900


<210> SEQ ID NO 2
<211> LENGTH: 12
<212> TYPE: PRT
<213> ORGANISM: Herpes simplex

<400> SEQUENCE: 2

Glu Gln Gly Ala Ser Thr Arg Asp Glu Gly Lys Gln
1               5                   10


<210> SEQ ID NO 3
<211> LENGTH: 360
<212> TYPE: DNA
<213> ORGANISM: Herpes simplex

<400> SEQUENCE: 3
```

-continued

```
gcctgtcccg tggggaccat ggatatccgg tagacgggca ggggagtctg caccgccgca     60

ttacggataa gcgccgcgat cgccgggggt gtggtgccct gctgttccgt ggcggccagt    120

ctcaggaggc gcttgacaat tccgcaggtc tgtgggggcg gcgtgccgcc cgccgtgtcc    180

tccccgggac tggcgggccc ccgtcgcggg tgtttgtgtt tgtttattcc gacattggtt    240

tatttaaata aacacagccg ttctgcgtgt ctgttcttgc gtgtggctgg gggcttatat    300

gtggggtccc gggggcggga tggggtttag cggcgggggg cggcgcgccg gacggggcgc    360
```

```
<210> SEQ ID NO 4
<211> LENGTH: 898
<212> TYPE: DNA
<213> ORGANISM: Herpes simplex

<400> SEQUENCE: 4

atacttttat ttattaactc acaggggcgc ttaccgccac aggaatacca gaataatgac     60

caccacaatc gcgaccaccc caaatacagc atggcgccac accacgccac aacagccctg    120

tcgccggtat ggggcatgat cagacgagcc gcgccgcgcg ttgggccctg tacagctcgc    180

gcgaattgac cctaggaggc cgccacgcgc ccgagttttg cgttcgtcgc tggtcgtcgg    240

gcgccaaagc cccggacggc tgttcggtcg aacgaacggc cacgacagtg gcataggttg    300

gggggtggtc cgacatagcc tcggcgggca ggcgctcgcg gaaacttaac acccacaccc    360

aacccactgt ggttctggct ccatgccagt ggcaggatgc tttcggggat cggtggtcag    420

gcagcccggg ccgcggctct gtggttaaca ccagagcctg cccaacatgg cacccccact    480

cccacgcacc cccactccca cgcaccccca ctcccacgca cccccactcc cacgcacccc    540

cactcccacg cacccccact cccacgcacc cccactccca cgcaccccca ctcccacgca    600

cccccactcc cacgcatccc cgcgatacat ccaacacaga cagggaaaag atacaaaagt    660

aaacctttat ttcccaacag acagcaaaaa tcccctgagt tttttttat tagggccaac    720

acaaaagacc cgctggtgtg tggtgcccgt gtctttcact tttcccctcc ccgacacgga    780

ttggctggtg tagtgggcgc ggccagagac cacccagcgc ccgaccccc cctccccaca    840

aacacggggg gcgtccctta ttgttttccc tcgtcccggg tcgacgcccc ctgctccc      898
```

```
<210> SEQ ID NO 5
<211> LENGTH: 900
<212> TYPE: DNA
<213> ORGANISM: Herpes simplex

<400> SEQUENCE: 5

atacttttat ttattaactc acaggggcgc ttaccgccac aggaatacca gaataatgac     60

caccactatc gcgaccaccc caaatacagc atggcgcccc accacaccac aacagccctg    120

tcgccggtat ggggcatgat cagacgagcc gcgcgctgcg cgttgggccc tgtacagctc    180

gcgcgaattg accctaggag gccgccacgc gcccgagttt tgcgttcgtc gctggtcgtc    240

gggcgccaaa gccccggacg gctgttcggt cgaacgaacg gccacgacag tggcataggt    300

tggggggtgg tccgacatag cctcggcggg caggcgctcg cggaaactta acacccacac    360

ccaacccact gtggttctgg ctccatgcca gtggcaggat gctttcgggg atcggtggtc    420

aggcagcccg ggccgcgact ctgtggttaa caccagagcc tgcccaacat gtcaccccca    480

ctcccacgca cccccactcc cacgcacccc cactcccacg cacccccact cccacgcacc    540

cccactccca cgcaccctca ctcccacgca ccctcactcc cacgcacccc cactcccacg    600
```

-continued

```
caccccact cccacgcacc cccgagatcc atccaacaca gacagggaaa agatacaaaa    660

gtaaaccttt atttcccaat agacagcaaa aatcccctga gttttttttt attagggcca    720

acactaaaga cccgctggtg tgtggtgccc gtgtctttca cttttcccct ccccgacacg    780

gattggctgg tgtagtgggc gcggccagag accacccagc gcccgacccc cccctcccca    840

caaacacggg gggcgtccct tattgttttc cctcgtcccg ggtcgacgcc ccctgctccc    900


<210> SEQ ID NO 6
<211> LENGTH: 12
<212> TYPE: PRT
<213> ORGANISM: Herpes simplex

<400> SEQUENCE: 6

Glu Gln Gly Ala Ser Thr Arg Asp Glu Gly Lys Gln
1               5                   10
```